(12) United States Patent
Kumar et al.

(10) Patent No.: US 6,447,295 B1
(45) Date of Patent: Sep. 10, 2002

(54) DIAMOND-LIKE CARBON COATED DENTAL RETAINING SCREWS

(75) Inventors: Ajay Kumar, Palmdale; Don Kennard, Huntington Beach, both of CA (US)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/550,675

(22) Filed: Apr. 17, 2000

Related U.S. Application Data
(60) Provisional application No. 60/129,766, filed on Apr. 15, 1999.

(51) Int. Cl.$^7$ ................................. A61C 13/12
(52) U.S. Cl. ......................... 433/172; 433/174
(58) Field of Search ................ 433/173, 174, 433/175, 176, 201.1

(56) References Cited

U.S. PATENT DOCUMENTS

| | | |
|---|---|---|
| 4,504,519 A | 3/1985 | Zelez |
| 4,790,753 A | 12/1988 | Fradera |
| 4,850,870 A | 7/1989 | Lazzara et al. |
| 4,855,026 A | 8/1989 | Sioshansi |
| 4,859,493 A | 8/1989 | Lemelson |
| 4,960,643 A | 10/1990 | Lemelson |
| 4,987,007 A | 1/1991 | Wagal et al. |
| 4,988,298 A | 1/1991 | Lazzara et al. |
| 5,006,068 A | 4/1991 | Lee et al. |
| 5,040,982 A * | 8/1991 | Stefan-dogar ............... 433/173 |
| 5,082,445 A | 1/1992 | Singer |
| 5,096,352 A | 3/1992 | Lemelson |
| 5,098,737 A | 3/1992 | Collins et al. |
| 5,104,318 A | 4/1992 | Piche et al. |
| 5,108,288 A | 4/1992 | Perry |
| 5,125,839 A | 6/1992 | Ingber et al. |
| 5,169,308 A | 12/1992 | Kvist |
| 5,181,850 A | 1/1993 | Neumeyer |
| 5,203,804 A | 4/1993 | Nikutowski et al. |
| 5,286,195 A | 2/1994 | Clostermann |
| 5,299,937 A | 4/1994 | Gow |
| 5,336,090 A | 8/1994 | Wilson, Jr. et al. |
| 5,344,318 A | 9/1994 | Wilson, Jr. et al. |
| 5,456,406 A | 10/1995 | Lemelson |
| 5,482,463 A | 1/1996 | Wilson, Jr. et al. |
| 5,527,182 A | 6/1996 | Willoughby |
| 5,571,016 A * | 11/1996 | Ingber et al. ............... 433/173 |
| 5,607,304 A | 3/1997 | Bailey et al. |
| 5,653,812 A | 8/1997 | Petrmichl et al. |
| 5,681,653 A | 10/1997 | Hammond et al. |
| 5,711,669 A | 1/1998 | Hurson |
| 5,725,573 A | 3/1998 | Dearnaley et al. |
| 5,731,045 A | 3/1998 | Dearnaley et al. |
| 5,733,122 A | 3/1998 | Gordon |
| 5,747,120 A | 5/1998 | McLean, II et al. |
| 5,763,072 A | 6/1998 | Kato et al. |
| 5,763,087 A | 6/1998 | Falabella |
| 5,763,879 A | 6/1998 | Zimmer et al. |
| 5,766,394 A | 6/1998 | Anderson et al. |
| 5,772,760 A | 6/1998 | Gruen et al. |
| 5,792,256 A | 8/1998 | Kucherov et al. |
| 5,799,549 A | 9/1998 | Decker et al. |
| 5,829,977 A | 11/1998 | Rogers et al. |
| 5,833,463 A | 11/1998 | Hurson |
| 5,879,161 A | 3/1999 | Lazzara |
| 5,919,043 A | 7/1999 | Weigl |
| 5,947,733 A * | 9/1999 | Sutter et al. ................ 433/173 |
| 5,989,026 A * | 11/1999 | Rogers et al. ............... 433/173 |
| 6,022,350 A | 2/2000 | Ganem |

FOREIGN PATENT DOCUMENTS

| | | |
|---|---|---|
| EP | 0 807 420 A1 | 11/1997 |
| GB | 966604 | 8/1964 |

OTHER PUBLICATIONS

"Super–Slick", *Mechanical Engineering,* John DeGaspari, pp. 46–48, Apr. 1999.

"Diamond Coated Total Hip Replacements", *Clinical Orthopaedics and Related Research,* Reijo Lappalainen, Asko Anttila and Harri Heinonen, No. 352, pp. 118–124, Jul. 1998.

"Development and Status of Diamondlike Carbon", *Synthetic Diamond: Emerging CVD Science and Technology,* A Wiley–Interscience Publication, Alfred Grill and Bernard S. Meyerson, pp. 91–96, 110–112,121,134–135, ©1994.

"Deposition of diamond–like carbon", *Thin Film Diamond,* Chapman & Hall, J. Robertson, pp. 107–109, ©1994.

"Atomic and Crystal Structures of Diamond", *Diamond Chemical Vapor Desposition,* Noyes Publications, Huimin Liu and David S. Dandy, pp. 8–9, ©1995.

"Raman Spectroscopy of Amorphous Carbon", *Covalently Bonded Disordered Thin–Film Materials,* Materials Research Society, Symposium proceedings vol. 498, D.R. Tallant, T.A. Friedmann, N.A. Missert, M.P. Siegal and J.P. Sullivan, p. 37, Dec. 2–4, 1997.

* cited by examiner

*Primary Examiner*—Todd E. Manahan
(74) *Attorney, Agent, or Firm*—Knobbe, Martens, Olson & Bear, LLP

(57) ABSTRACT

The invention relates to a coated dental screw for retaining and securing components of a dental prosthetic implant stack. The screw is coated with a hard carbon coating/film to provide a low friction surface finish which advantageously results in improved preloading of the screw, and hence a high clamping force between the components of the dental prosthetic implant stack. The coating can comprise diamond-like carbon (DLC), amorphous diamond, crystalline diamond, or a combination thereof. The dental screw can include abutment retaining screws and prosthesis retaining screws. Other advantages provided by the hard carbon coating include high mechanical surface hardness, biocompatibilty, corrosion resistance, chemical inertness and low cost.

58 Claims, 11 Drawing Sheets

DIAMOND-LIKE CARBON COATED DENTAL RETAINING SCREWS

RELATED APPLICATIONS

This application claims the benefit of U.S. Provisional Application No. 60/129,766, filed Apr. 15, 1999.

BACKGROUND OF THE INVENTION

1. Field of the Invention

The present invention relates generally to dental prosthetics, and more particularly to retaining screws to secure dental components, such as an abutment and/or prosthesis to a dental implant or fixture.

2. Description of the Related Art

In restorative dental implantology, an artificial root or "fixture" is surgically implanted into the jawbone of a patient. The implant is typically formed of titanium or a commercially pure titanium alloy. Titanium, and its biocompatible alloys, referred to herein simply as titanium, is the material of choice for surgical implants because it offers a combination of nearly ideal characteristics—high strength, light weight, bio-compatibility and essentially total resistance to corrosion in contact with tissues and bones.

After implanting and following an initial healing period of a few months, new bone growth is observed to occur around the titanium fixture supporting it securely in place. This process is known as osseointegration. In a secondary procedure, an abutment of a specific desired size and shape is then placed over the fixture and secured thereto by a bolt threaded into a cavity in the fixture. Typically, a titanium bolt is used, called the abutment retaining screw. The prosthesis is the third component of the system and may be fabricated of cast gold alloy and porcelain. However, since machined parts have greater accuracy than cast parts, the prosthesis is commonly cast to a machined component which is fastened to a threaded cavity in the abutment by a retaining screw.

Alternative approaches include attaching the prosthesis directly to the fixture without any intervening abutment. This method uses only one titanium retaining screw. A further variation includes cementing the restoration to the implant and/or abutment in a similar manner as is done in conventional fixed bridges on natural teeth. Typically, in this case, a tapered abutment without threads, often referred to as a cementable abutment, is fastened to the fixture with a titanium abutment retaining screw. This method also utilizes only one screw in the system.

Thus, implant dentistry relies upon one or more screws to fasten together component stacks. These components typically include fixtures, abutments and artificial teeth though they can include other components, for example, impression copings. Retaining screws have been used in dental prostheses for more than two decades and the problems inherent with screw securement have been studied in depth.

Typically, a special torque wrench is used to torque the abutment screw to the desired load or torque. However, the torque wrench measures total torque resistance only. As the abutment screw is turned, resistance increases indicating rising torque values on a dial gauge. But only part of this resistance comes about by the tension forces which are created as the abutment screw stretches under an applied load. The resistance forces which produce the clamping force are equal in magnitude and opposite in direction to the stretching force (tensile load). The important parameter of interest, however, is the resulting clamping load, which is produced when the screw is tightened at various torque values. As, noted above, this is a small component of the overall torque applied to a titanium screw, due to the large friction forces involved.

Thus, it is desirable to provide a high preload to the abutment screw so that the dental restoration can withstand the applied loads, and hence prevent joint failure and also to prevent screw loosening. Screw loosening generally occurs due to a "ratcheting" effect as significant loads, for example, during mastication, are repeatedly applied to the dental restoration, and causes the screw threads to turn or "back off" in steps. As the screw loosens, the preload decreases and this renders the implant-abutment joint further susceptible to failure.

The high loads encountered by the abutment screw can also cause the contacting surfaces of the components to open slightly on one side of the implant system by bending of the screw. This can create small gaps between the opposed surfaces of the abutment and the implant. Undesirably, oral fluids may gain access to the interior of the implant system through the gaps, thus risking infection. Movement of the implant components may also cause the screws to loosen or fail as they are repeatedly stretched and bent.

U.S. Pat. No. 5,482,463 to Wilson, et al. describes a screw joint for dental implant component stacks which has greater resistance to loosening, and therefore greater resistance to bending and/or breaking. This is accomplished by the use of spring washers and has the effect of increasing the preload and of increasing resistance to slippage of the entire joint. While the use of springs, as described by Wilson, et al. provides a partial solution to the long-standing problem of loosening of screws in dental implants, the fundamental problem of low preloading remains largely unsolved.

U.S. Pat. No. 5,711,669 to Hurson, incorporated by reference herein, teaches a system for improving the tightening efficiency of a titanium abutment screw using a malleable material, such as gold or silver, that is both biocompatible and has a low coefficient of friction. However, such coatings are expensive and, in some cases, can reduce the friction to such an extent that the screws can be easily over-torqued by the dental practitioner applying only minimal torque. Moreover, the malleability of the coating can render the threads of the titanium screw susceptible to galling.

SUMMARY OF THE INVENTION

Accordingly, it is an object and advantage of the prevent invention to overcome some or all of the above limitations by providing an amorphous "hard carbon" coated retaining screw for a dental prosthetic implant system. Though there are a wide variety of commercially available "hard carbon" coatings and some of the properties of hard carbon as a surface coating are known in the art, the present invention provides certain novel and unique benefits and advantages over the prior art in the field of screw retained prosthetic constructions particularly in the field of oral restorations, and more particularly in the field of dental screws for retaining abutments and/or dental restorations as related to the stacking and assembly of dental components.

The hard carbon coating provides a low friction surface finish which advantageously results in improved preloading of the screw, and hence a high clamping force between the components of the dental prosthetic implant system. The coating can comprise diamond-like carbon (DLC), amorphous diamond, crystalline diamond, or a combination thereof. The dental screw can include abutment retaining screws and prosthesis retaining screws. Other advantages provided by the hard carbon coating include high mechanical surface hardness, biocompatibilty, corrosion resistance, chemical inertness and low cost.

In accordance with one embodiment of the present invention, a retaining screw for fastening a dental component to an implant is provided. The implant has osseointegrated in a jawbone. The retaining screw generally comprises a head and a shank. The screw head comprises a seating surface sized and configured to engage a seating surface of the dental component. The screw head further comprises a cavity adapted to receive a tool for tightening the screw. The shank is in mechanical communication with the head and comprises threads adapted to threadably engage a threaded socket of the implant. A coating of hard carbon is applied to the seating surface of the screw head and to at least a portion of the shank. This reduces friction during tightening of the retaining screw and improves the preloading of the screw.

In accordance with another embodiment of the present invention, a dental implant system for supporting a prosthesis is provided. The dental implant system generally comprises a retaining screw, a dental implant and an abutment. The retaining screw generally comprises a head and a shank. The screw head comprises a seating surface and a cavity adapted to receive a tool for tightening the screw. The shank is in mechanical communication with the head and comprises threads. A coating of hard carbon is applied to the seating surface of the screw head and to at least a portion of the shank. The dental implant comprises a root portion and a threaded socket engaged with the threads of the retaining screw. The abutment is substantially irrotationally coupled with the implant and comprises a seating surface. The seating surface of the abutment is engaged with the seating surface of the head of the retaining screw. Advantageously, the hard carbon coating permits fastening of the abutment to the dental implant with an increased clamping force.

In accordance with one embodiment of the present invention, an abutment securement system to fasten dental components in a stack is provided. The abutment securement system comprises a film of diamond-like carbon (DLC) applied to a seating surface of a screw and/or to a seat of an abutment. Advantageously, this reduces friction between the seating surface and the seat, and thereby provides improved preloading of the screw.

In accordance with another embodiment of the present invention, a dental implant stack for supporting an oral restoration is provided. The dental implant stack generally comprises an implant, an abutment and a dental screw. The implant comprises a body portion adapted to be received in an alveolar cavity and an internal threaded bore. The abutment comprises a through cavity having a shoulder formed therein and is seated on the implant. The dental screw comprises a threaded portion engaged with the threaded bore of the implant and a cap having a seating surface abutting against the shoulder of the abutment. A coating of amorphous hard carbon is provided on the seating surface of the dental screw to reduce friction. Desirably, this provides a high clamping force between the implant and the abutment.

In accordance with yet another embodiment of the present invention, a dental prosthetic assembly is provided. The dental prosthetic assembly generally comprises a dental implant, a dental component and a securement bolt. The dental implant is osseointegrated in a jawbone and has a threaded socket originating from a top end. The dental component is in abutting contact with the implant and has an internal seating surface. The securement bolt has a threaded portion engaged with the threaded socket of the implant. A film comprising amorphous diamond is provided on the threaded portion of the securement bolt and/or the threaded socket of the implant. This reduces the coefficient of friction between the threaded portion of the securement bolt and the threaded socket of the implant.

In accordance with a further embodiment of the present invention, a dental prosthetic implant system for supporting an artificial tooth is provided. The dental prosthetic implant system generally comprises an implant, an abutment, a washer and a screw. The implant has a post at a top end and a threaded bore originating therefrom. The abutment has an internal passage with a shoulder therein and a socket at a bottom end substantially irrotationally engaged with the post of the implant. The washer is seated on the shoulder of the abutment passage and has a conical seating surface. The screw comprises a threaded portion engaged with the threaded bore of the implant and a head having a tapered surface abutting against the conical seating surface of the washer. This resists or reduces the tendency of screw loosening.

In accordance with one embodiment of the present invention, a method of forming a dental stack for supporting a prosthesis is provided. The method comprises the step of placing a first dental component having an internal cavity on a second dental component having a threaded bore. A retaining screw is inserted through the cavity of the first dental component to threadably engage the threaded bore of the second dental component. The retaining screw has a coating of hard carbon formed thereon to reduce friction. The retaining screw is then tightened to a predetermined or preselected torque to fasten the first dental component to the second dental component.

In accordance with another embodiment of the present invention, a method of increasing the preload on a screw used to secure dental components is provided. The method comprises the step of seating a dental component on an implant. The dental component has an internal shoulder. The implant has a threaded socket and is osseointegrated in a jawbone. A screw is threaded in the threaded socket of the implant and the head of the screw is seated against the shoulder of the dental component. The head of the screw and/or the shoulder of the dental component have/has a diamond-like carbon coating to reduce friction. The screw is then torqued using a tool to a predetermined or preselected load.

In accordance with yet another embodiment of the present invention, a method of making a retaining screw for securing and assembling dental components in a stack is provided. The method comprises the step of providing a cap portion on the retaining screw so that the cap portion has a seating surface and a cavity adapted to receive a tool for tightening the screw. A shank portion is provided on the retaining screw so that the shank portion has threads thereon. An amorphous hard carbon coating is formed on at least the seating surface of the cap portion to provide improved preloading.

For purposes of summarizing the invention and the advantages achieved over the prior art, certain objects and advantages of the invention have been described herein above. Of course, it is to be understood that not necessarily all such objects and advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

DETAILED DESCRIPTION OF THE PREFERRED EMBODIMENTS

Figure 1:
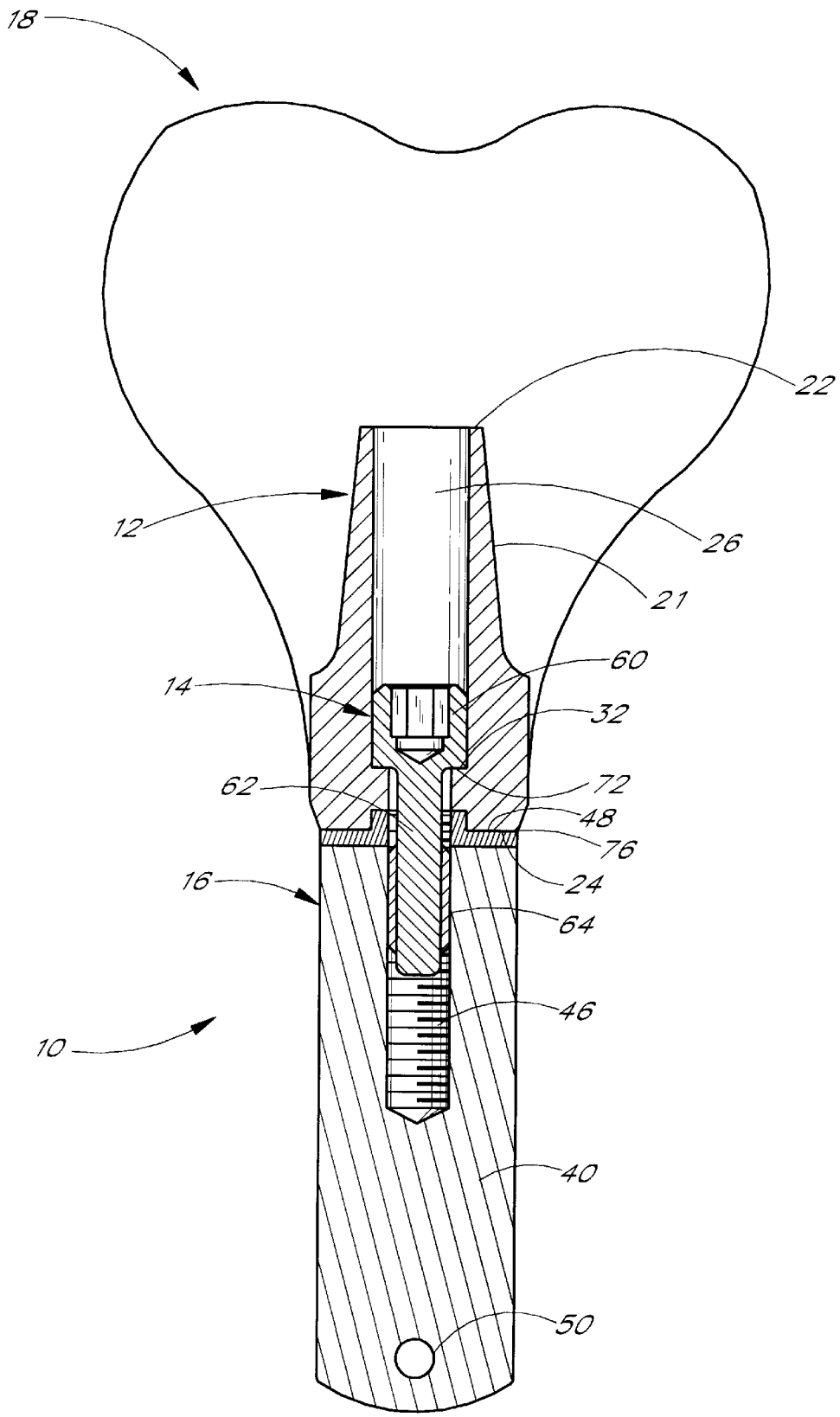
FIG. 1 is a partial cross-section view of a dental implant system supporting a prosthesis and having features in accordance with one preferred embodiment of the present invention.

As a screw is threaded into a prethreaded bore, the screw is tensioned between the engaging threaded surfaces of the screw and the bore, and the abutting surfaces of the screw head and the stationary seating surface around the bore. After the screw head seats on a stationary surface, the tension on the screw increases as the screw is threaded farther into the bore. This tension on the screw produces a force that is commonly referred to as the "preload" of the screw.

Thus, when a screw is tightened, a tensile force, termed the "preload" is built up in the screw. The screw is placed in tension, and the components fastened by the screw are placed in compression. The preload holds the components of an implant component stack together by producing a clamping force. It is desirable that the preload be high and fluctuate as little as possible to prevent joint failure and screw loosening.

Classical screw theory relates the degree (angle) of turn of a screw to preload or clamping force by the following simplified equation:

$$F = \left(\frac{P\theta}{360}\right)K$$

where:
F=preload or clamped force of the two parts held together by the screw (e.g., the abutment to the implant),
P=pitch of the abutment screw (e.g., 0.4 mm for a typical abutment screw),
θ=degree (angle) of turn measured after snugging of the screw head against the opposed surface (i.e., the abutment/implant surfaces are seated together), and
K=spring constant of the screw and joint.

If the degree of turn (θ) is increased, the resulting clamping force or preload (F) is also increased. An increase in the clamping force results in a tighter abutment/implant joint. The tighter joint imparts greater resistance to screw loosening and increases the load required to pry the abutment/implant joint apart. Side loads produced during mastication result in forces that tend to pry the abutment/implant joint apart. Joint prying and fatigue strength are directly related and, thus, the greater the force required to pry the joint, the greater the force required to cause cyclic fatigue failure of the screw.

In general, the fatigue strength of the screw increases as the preload increases because the screw remains more stable when subjected to various loads. The farther a screw is threaded into its bore after seating of the screw head, the greater the preload on the screw, that is, the greater the force exerted by the inherent resilience (elastic recovery) of the screw itself on the opposing surfaces responsible for the tension on the screw. Advancing movement of the screw into its bore is resisted in part by the friction between the rotating surfaces of the screw and the opposed stationary surfaces, which must be overcome by the applied torque to advance the screw.

For any screw to serve its purpose of securing one or more components together, it must be tightened or torqued to provide the desired retention force. However, titanium and many other metals and alloys have a high coefficient of friction. For example, during the tightening of a titanium abutment screw, approximately 50% of the applied torque is spent overcoming the mating friction under the head, about 40% is spent overcoming friction resistance in the threads, and only approximately 10% of the total torque exerted produces the desired tension (stretching) in the abutment screw.

Titanium and most metals behave elastically within a wide range of applied loads. The elasticity property which allows an abutment screw to return to its initial length upon unloading ceases at the yield point of the material. If the abutment screw is tightened above the yield point, a permanent elongation starts to set in prior to reaching the maximum strength which the abutment screw can sustain. As the result of such behavior, the clamping force, which is produced from the tension as torque is applied, increases proportionally faster in the elastic range. Above the yield point, the rate of increase of the clamping force diminishes with increased loading, since additional tightening energy is spent in the permanent stretching of the screw. If tightening proceeds further, a maximum torque value will be attained, followed by a sharp decrease in torque as additional turning is attempted. The decrease in the torque is an indication of loss of preload as the abutment screw deforms and the maximum or ultimate strength of the screw is exceeded.

Thus, it is desirable that an abutment screw be tightened to a load just below the yield point to provide maximum or optimum tensile strength and preload. The load levels at which yield occurs is different for each material or alloys of the same material. Generally, as the strength of the material increases, the yield point increases correspondingly, meaning that an abutment screw's ability to carry higher loads is increased. For example, an abutment screw fabricated from the titanium alloy (Ti-6Al-4V) will have a higher yield point than an abutment screw made out of CP titanium, and hence can be tightened to a higher torque to carry greater loads.

Another issue is the assembly load that is to be sustained by the mating members (implant and abutment). The fastening member (abutment screw) should preferably be tightened to a load that exceeds the peak carrying load of the assembly, otherwise the fastening parts (implant and abutment) might either fail during the installation or subsequently during use in the patient's mouth. Usually, a load is either static (clinching) or dynamic (during mastication) where the joint load is acting either in shear or in tension. When an abutment screw is tightened, the resulting load exerted by the abutment screw should exceed the expected implant-abutment assembly load, so that the preload of the abutment screw can sustain the assembly load.

Figure 2:
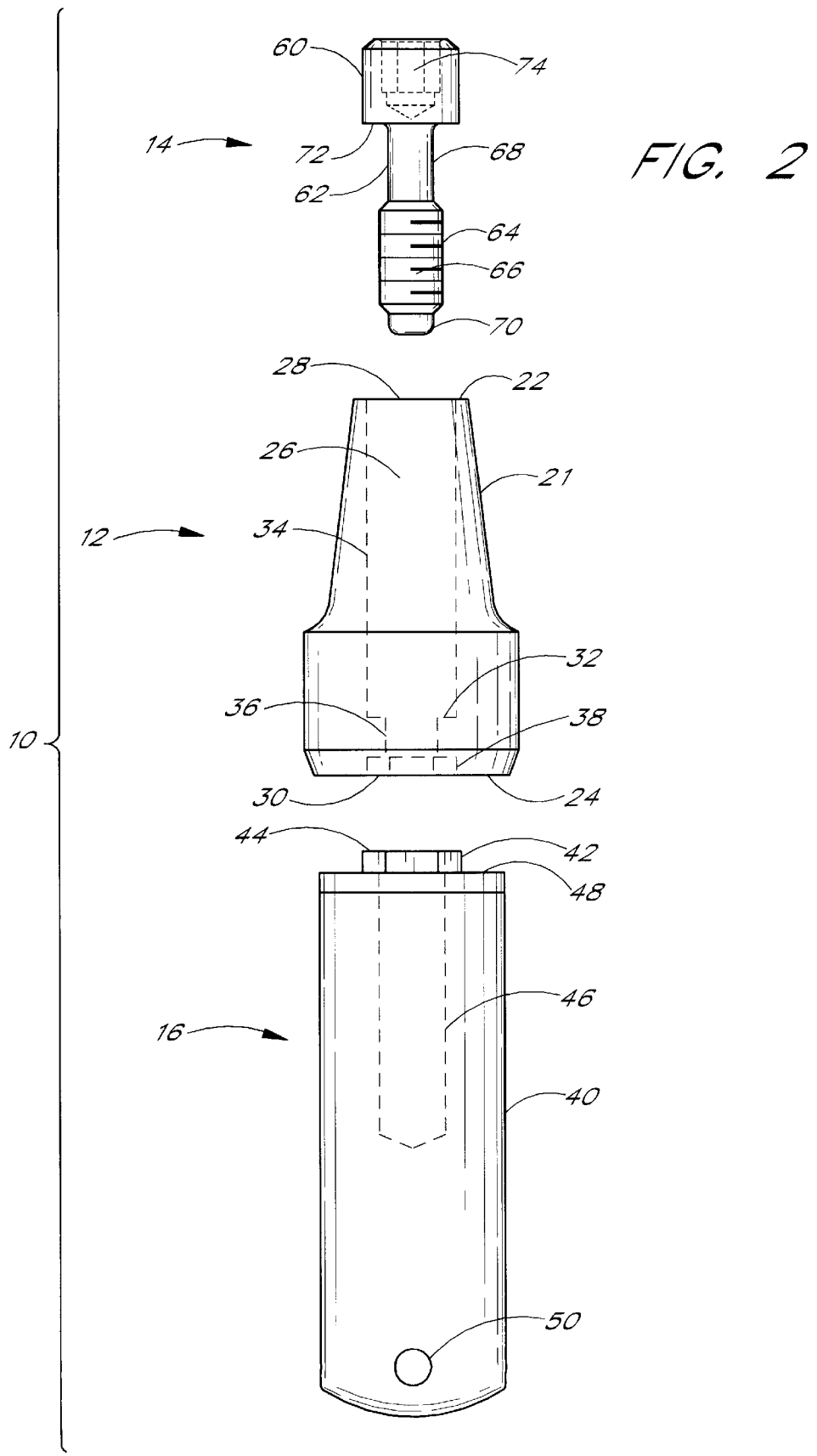
FIG. 2 is an exploded front elevation view of the dental implant system of FIG. 1.

FIGS. 1 and 2 illustrate a dental prosthetic implant system, assembly, stack or combination 10 having features in accordance with one preferred embodiment of the present invention. The dental implant system 10 generally comprises an abutment 12, an abutment retaining screw or bolt 14, and a dental implant, fixture or root 16. The dental implant 16 is adapted to be received in a hole, osteotomy or alveolar cavity in the jawbone of a patient. The abutment retaining screw 14 serves the purpose of fastening the abutment 12 to the implant 16. The abutment 12 and abutment retaining screw 14 can be commercialized as a dental kit or a dental securement system. The dental kit may further include additional associated components.

In one preferred embodiment, the dental implant system 10 further comprises a dental restoration, prosthesis or artificial tooth 18. The abutment 12 supports the restoration 18 in the mouth of a patient. The prosthesis 18 can be cemented to the abutment 12. Alternatively, or in addition, a screw or bolt is utilized to mount and retain the prosthesis on the abutment 12.

Figure 3:
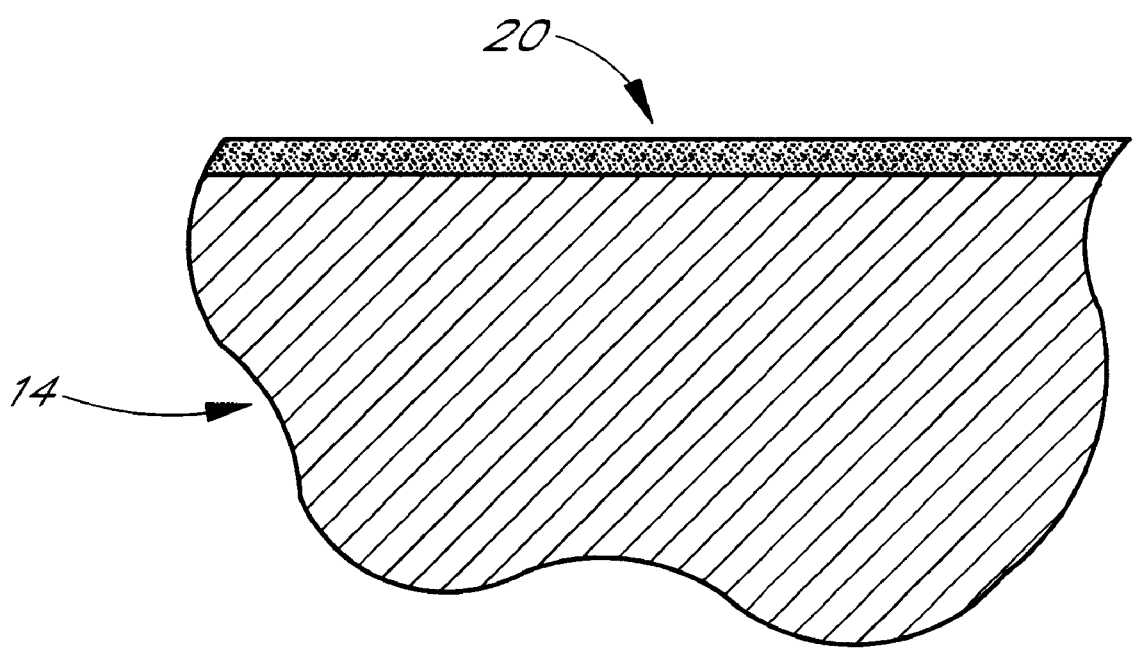
FIG. 3 is a schematic illustration of one preferred coating (not to scale) on a retaining screw of the dental implant system of FIG. 1.
Figure 5:
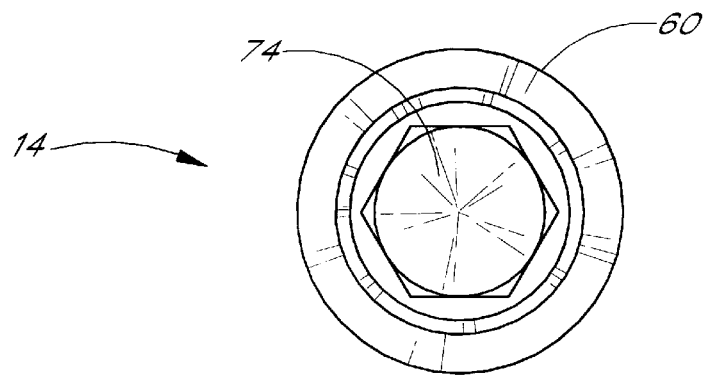
FIG. 5 is a top plan view of the retaining screw of FIG. 4.
Figure 4:
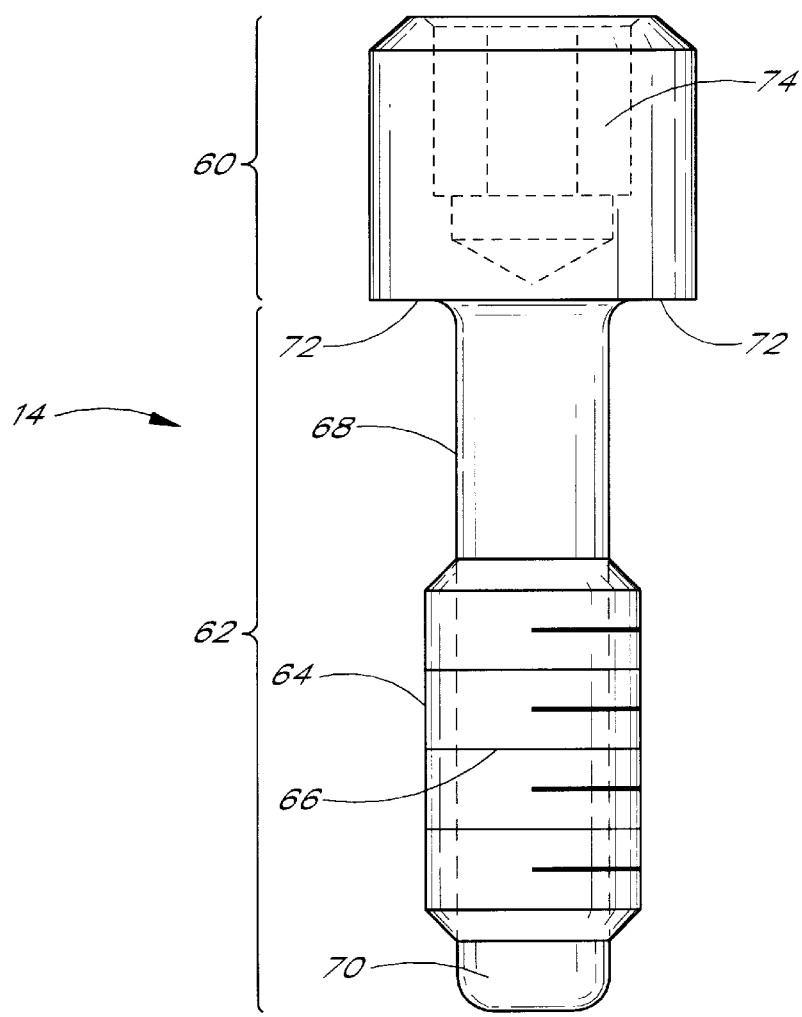
FIG. 4 is a front elevation view of a retaining screw of the dental implant system of FIG. 1 having features in accordance with one preferred embodiment of the invention.

In one preferred embodiment, at least a portion of the dental retaining screw 14 and/or a mating portion of the abutment 12 is coated with an amorphous hard carbon coating or film 20, as schematically illustrated in FIG. 3. The coating 20 can comprise, for example, a diamond-like carbon (DLC) coating 20, an amorphous diamond coating 20, a crystalline diamond coating 20, or a combination thereof. The coating 20 can be multi-layered and comprise one or more layers. The term "hard carbon," as used herein, can denote any or all of the above giving due consideration to achieving some or all of the benefits and advantages of the present invention.

In one preferred embodiment, the coating 20 (FIG. 3) is a diamond-like carbon (DLC) coating 20. In another preferred embodiment the coating 20 comprises an amorphous diamond coating 20. Generally, diamond-like carbon (DLC) is hydrogenated and this feature distinguishes it from amorphous diamond which has a negligible proportion of hydrogen. Both comprise an amorphous arrangement of atoms and a major or substantially sizable proportion of $sp^3$ bonding which results in low friction, high mechanical hardness, chemical inertness, and other desirable properties. Diamond-like carbon (DLC) and amorphous diamond can also include some degree of $sp^2$ bonding.

In general, the "hard carbon" coating 20 of the present invention comprises (a) at least some $sp^3$ bonding, (b) some, negligible or no $sp^2$ bonding, and (c) some, negligible or no hydrogenation. A discussion of $sp^n$ bonding configurations is available in many references, for example, "Synthetic Diamond: Emerging CVD Science and Technology," edited by K. E. Spear and J. P. Dismukes (sponsored by the Electrochemical Society, Inc.), Wiley, N.Y., 1994. Though there are a wide variety of commercially available "hard carbon" coatings and some of the properties of hard carbon as a surface coating are known in the art, the present invention provides certain novel and unique benefits and advantages over the prior art in the field of screw retained prosthetic constructions particularly in the field of oral restorations, and more particularly in the field of dental screws for retaining abutments and/or dental restorations as related to the stacking and assembly of dental components.

As discussed in greater detail later herein, one advantage of the coating 20 (FIG. 3) is that it provides a reduced coefficient of friction (increased lubriciousness) between the contacting surfaces of a screw and the components being assembled, and hence results in a higher "preload" or clamping force between the components. Some of the other benefits and advantages arise as a consequence of the coating 20 properties of high surface hardness, corrosion resistance, chemical inertness, biocompatiblity and low cost. Some or all of these desirable properties of the hard carbon coating 20 translate into improved retention force for a given torque, reduced tendency to screw loosening and joint failure over time, improved stability of the dental implant system, increased screw fatigue life and reduced risk of infection.

The abutment 12 (FIGS. 1 and 2) is generally elongated in shape and can have a variety of shaped exterior surfaces 21 adapted to seat the prosthesis 18. For example, the abutment exterior surface 21 can be tapered, conical, cylindrical, straight, angled, contoured, and combinations thereof, among others, as required or desired, giving due consideration to the goals of supporting a prosthesis, and/or of achieving one or more of the benefits and advantages as taught or suggested herein.

As the skilled artisan will recognize, the present invention can be embodied utilizing a wide variety of commercially available abutments. Thus, the abutment 12 can comprise, for example, the UCLA abutment and healing abutments, as required or desired, giving due consideration to the goals of achieving one or more of the benefits and advantages as taught or suggested herein.

The abutment 12 has a top end 22, a bottom seating end/surface 24 for interfacing or abutting with the implant 18, and a through cavity or bore 26 with a generally circular opening 28 at the top end 22 and a generally hexagonal opening 30 at the bottom end 24. The cavity 26 is adapted to receive the retaining screw 14 and includes an internal seating surface, shoulder, seat or ledge 32 which serves as a seating surface for the head of the screw 14. Preferably, the shoulder 32 is generally annular or ring-like in shape. In other preferred embodiments, the shoulder 32 and/or cavity 26 can be efficaciously configured and dimensioned in alternate manners, as required or desired, giving due consideration to the goals of providing a seating surface for the screw 14, receiving the screw 14, and/or of achieving one or more of the benefits and advantages as taught or suggested herein.

The shoulder or abutting surface 32 divides or partitions the through cavity 26 into an upper generally cylindrical cavity, portion or surface 34 and a lower (or middle) generally cylindrical cavity, portion or surface 36. The cavity 34 and cavity 36 are in communication with one another with the cavity 34 having a diameter larger than that of the cavity 36.

The cavity 36 is further in communication with a generally hexagonal socket, portion or surface 38 at the bottom end 24 of the abutment 12. The hexagonal socket 38 permits generally irrotational mating, coupling or attachment between the abutment 12 and implant 16. The socket 38 may be alternately shaped with efficacy, as required or desired, giving due consideration to the goals of providing substantially irrotational mating between the abutment 12 and the implant 16, and/or of achieving one or more of the benefits and advantages as taught or suggested herein.

The implant 16 (FIGS. 1 and 2) can any be one of a wide variety of dental implants, for example, a threaded implant, a cylindrical implant, a tapered implant, as are known in the art. The implant 16 comprises a body or root portion 40 adapted to engage an osteotomy or alveolar cavity in the jawbone of a patient and a generally hexagonal post or protrusion 42 at a top end 44. A blind internal threaded socket or bore 46 originates from the top end 44 and into the implant body portion 40. The threaded socket 46 is adapted to threadably engage the abutment retaining screw 14. A seating surface 48 generally circumscribes the hexagonal post 42 to engage, contact or abut against the opposing abutment seating surface 24. The implant body portion 40 may include a passage 50 formed therethrough to permit in-growth of bone and tissue for locking or anchoring the implant 16 in the osteotomy.

The implant hexagonal post 42 is configured to substantially irrotationally mate with the abutment hexagonal socket 38. The post 42 may be alternately shaped with efficacy, as required or desired, giving due consideration to the goals of providing substantially irrotational mating between the abutment 12 and the implant 16, and/or of achieving one or more of the benefits and advantages as taught or suggested herein. Alternatively, a mating post may be provided at the bottom end of the abutment 12 to interlock with a corresponding mating socket at the top end of the implant 16 with efficacy, as required or desired, giving due consideration to the goals of providing substantially irrotational mating between the abutment 12 and the implant 16, and/or of achieving one or more of the benefits and advantages as taught or suggested herein.

The abutment retaining screw 14 ( FIGS. 1–2 and 4–5) is generally dimensioned and configured to adapt to a particular implant-abutment pair. The securing screw 14 generally comprises an upper head or cap portion 60 in mechanical communication with a shank portion 62. The shank 62 comprises a threaded portion 64 having threads 66 adapted to threadably engage the threaded socket 46 of the implant 16. The threaded portion 64 is in mechanical communication with an upper non-threaded portion 68 and a lower non-threaded portion 70 of the shank 62. In other preferred embodiments, the shank 62 can be efficaciously configured and dimensioned in alternate manners, as required or desired, giving due consideration to the goals of securing the abutment 12 and implant 16, and/or of achieving one or more of the benefits and advantages as taught or suggested herein.

The screw head 60 is preferably generally cylindrical in shape. In other preferred embodiments, the screw head 60 can be efficaciously configured and dimensioned in alternate manners, as required or desired, giving due consideration to the goals of securing the abutment 12 and implant 16, and/or of achieving one or more of the benefits and advantages as taught or suggested herein.

The screw head 60 includes a lower contacting, seating or abutting surface 72 for engaging the opposed seating surface or shoulder 32 of the abutment 14. Preferably, the contacting surface 72 is generally annular or ring-like in shape to generally conform to the shape of the abutment shoulder 32. In other preferred embodiments, the contacting surface 72 can be efficaciously configured and dimensioned in alternate manners, as required or desired, giving due consideration to the goals of securing the abutment 12 and implant 16, and/or of achieving one or more of the benefits and advantages as taught or suggested herein.

The screw head 60 preferably has a generally hexagonal cavity or socket 74 for receiving a torque wrench or other suitable tool. In other preferred embodiments, the socket 74 can be efficaciously configured in a wide variety of alternate manners, as required or desired, giving due consideration to the goals of receiving a suitable tool, and/or of achieving one or more of the benefits and advantages as taught or suggested herein.

As indicated above, and referring to FIGS. 1–5, preferably, at least a portion of the dental screw or bolt 14 is coated with a diamond-like carbon (DLC) coating or film 20 (FIG. 3) to advantageously provide a low friction surface finish which desirably reduces the wastage of applied torque during screw tightening. Preferably, the coating 20 is formed by a physical vapor deposition (PVD) and/or chemical vapor deposition (CVD) technique, though other coating techniques may be utilized with efficacy, as required or desired, giving due consideration to the goals of providing a hard carbon coating on a dental screw or component, and/or of achieving one or more of the benefits and advantages as taught or suggested herein.

In one preferred embodiment, the screw head seating surface 72 and the entire m screw shank 62 are coated with a diamond-like carbon (DLC) coating 20. In another preferred embodiment, the screw head seating surface 72 and the screw threaded portion 64 are coated with a diamond-like carbon (DLC) coating 20. In yet another preferred embodiment, the entire screw 14 is coated with a diamond-like carbon (DLC) coating 20. In other preferred embodiments, various combinations of selected surfaces of the dental screw 14 can be coated with diamond-like carbon (DLC) with efficacy, as required or desired, giving due consideration to the goals of providing increased preload, and/or of achieving one or more of the benefits and advantages as taught or suggested herein.

In one preferred embodiment, the screw head seating surface 72 and the entire screw shank 62 are coated with an amorphous diamond coating 20. In another preferred embodiment, the screw head seating surface 72 and the screw threaded portion 64 are coated with an amorphous diamond coating 20. In yet another preferred embodiment, the entire screw 14 is coated with an amorphous diamond coating 20. In other preferred embodiments, various combinations of selected surfaces of the dental screw 14 can be coated with amorphous diamond with efficacy, as required or desired, giving due consideration to the goals of providing increased preload, and/or of achieving one or more of the benefits and advantages as taught or suggested herein.

In general, a hard carbon coating or film, such as the diamond-like carbon (DLC) coating 20 (FIG. 3), may be applied to selected surfaces of the screw 14, the abutment 12 and/or the implant 16 in a variety of configurations, as required or desired, giving due consideration to the goals of providing increased preload, and/or of achieving one or more of the benefits and advantages as taught or suggested herein. For example, the hard carbon coating 20 may be provided on the seating surface 32 of the abutment 12 and/or the threaded bore 46 of the implant 16 instead of on the abutment screw 14 or in conjunction with the hard carbon coating 20 on the screw 14. Those of ordinary skill in the art will appreciate that the hard carbon coating 20 can also be provided on selected surfaces of abutments which comprise built in threaded portions, and hence do not utilize a separate retaining screw.

In one preferred embodiment, and referring to FIG. 3, the hard carbon coating 20 has a thickness of about 1 micron ($\mu$m). In another preferred embodiment, the hard carbon coating 20 has a thickness in the range from about 0.5 $\mu$m to about 2.5 $\mu$m. In yet another preferred embodiment, the hard carbon coating 20 has a thickness in the range from about 0.1 $\mu$m to about 10 $\mu$m. In other preferred embodiments, the thickness of the hard carbon coating 20 may be efficaciously selected, as required or desired, giving due consideration to the goals of providing increased preload, and/or of achieving one or more of the benefits and advantages as taught or suggested herein.

As indicated above, the hard carbon coating 20 (FIG. 3) comprises at least some, and preferably, a major or substantially sizable proportion of $sp^3$ chemical bonding. In one preferred embodiment, the hard carbon coating 20 comprises between about 70% to about 100% $sp^3$ bonding. In other preferred embodiments, the coating 20 can comprise less $sp^3$ bonding, as required or desired, giving due consideration to the goals of providing increased preload, and/or of achieving one or more of the benefits and advantages as taught or suggested herein.

Also, as indicated above, the hard carbon coating 20 (FIG. 3) in one preferred embodiment comprises diamond-like carbon (DLC) which includes some hydrogenation. In one preferred embodiment, the hydrogen content of the hard carbon or DLC coating 20 is between about 5 to about 35 atomic %. In other preferred embodiments, the hydrogen content can be less or more, as required or desired, giving due consideration to the goals of providing increased preload, and/or of achieving one or more of the benefits and advantages as taught or suggested herein.

In general, the present invention can be used to adjust some of the properties of the hard carbon coating 20 (FIG. 3) by varying the relative proportions of $sp^3$ and $sp^2$ bonding, and the hydrogen content. These properties can include the friction coefficient, mechanical hardness, corrosion resistance, and chemical inertness, among others. In this manner, by "tweaking" the bonding and/or chemical structure of the hard carbon coating 20, it may be possible to customize the coating 20 to optimally adapt to a particular dental application or implant system by providing a synergistic balance between one or more desirable properties of the hard carbon coating 20.

In one preferred embodiment, the hard carbon coating 20 (FIG. 3) provides a coefficient of friction of about 0.15 between the contacting surfaces. In another preferred embodiment, the hard carbon coating 20 provides a coefficient of friction in the range from about 0.1 to about 0.2 between the contacting surfaces. In yet another preferred embodiment, the hard carbon coating 20 provides a coefficient of friction in the range from about 0.05 to about 0.25 between the contacting surfaces. In other preferred embodiments, the hard carbon coating can have a lower or higher coefficient of friction, as needed or desired, giving due consideration to the goals of providing high preload, and/or of achieving one or more of the benefits and advantages as taught or suggested herein. (It should be noted that a typical value of the coefficient of friction between uncoated titanium surfaces is about 0.5.)

In one preferred embodiment, the hard carbon coating 20 (FIG. 3) has a Knoop hardness of about 2000 kg/mm$^2$. In other preferred embodiments, the hard carbon coating 20 can have a lower or higher mechanical surface hardness, as needed or desired, giving due consideration to the goals of providing suitable durability, and/or of achieving one or more of the benefits and advantages as taught or suggested herein.

As indicated above, the hard carbon coating 20 (FIG. 3) can comprise a wide variety of commercially available "hard carbon" coatings including, but not being limited to, diamond-like carbon (DLC), amorphous diamond, crystalline diamond, or a combination thereof. For example, if the inclusion of a certain proportion of crystalline structure is advantageous for a particular dental application or implant system, the coating 20 may include a certain quantity of crystalline diamond along with diamond-like carbon (DLC) and/or amorphous diamond. Also, the coating 20 may be doped with small quantities of other materials to achieve a desired result or goal.

The hard carbon coating 20 (FIG. 3) can be formed by a variety of techniques, for example, physical vapor deposition (PVD) processes and chemical vapor deposition (CVD) processes. The physical vapor deposition (VD) may comprise single-ion beam sputtering, dual ion-beam sputtering, and radio-frequency (RF) sputtering, among others. The chemical vapor deposition (CVD) may include hot-filament CVD, plasma-assisted CVD (PACVD), direct-current (DC) PACVD, radio-frequency (RF) PACVD, direct-current (DC) thermal plasma (CVD), radio-frequency (RF) thermal plasma CVD, and flame CVD, among others.

It is desirable to clean and passivate the surface of the dental screw 14 (FIGS. 1–2 and 4–5) prior to applying the coating 20 (FIG. 3). This facilitates better adherence of the hard carbon coating 20 to the passivated surface of the screw 14. Preferably, this cleaning process utilizes ultrasonic cleaning followed by a plasma cleaning of the screw 14. The plasma cleaning step includes bombardment of the screw 14 by suitable ions, such as argon ions.

In one preferred embodiment, a combination of physical vapor deposition (PVD) and chemical vapor deposition (CVD) techniques is used to form the hard carbon coating 20 on selected surfaces of the screw 14. The cleaning process and application of the coating can be performed by any one of a number of commercial coating providers. If needed or desired, one or more intermediate layers may be formed on the retaining screw 14, for example, to facilitate better adherence of the coating 20.

The dental screw 14 is preferably manufactured by machining operations and techniques. In other preferred embodiments, as the skilled artisan will recognize, the retaining or securement screw 14 can be manufactured by casting, forging and/or molding, among other known manufacturing technologies.

The retaining or securement screw 14 is preferably formed of titanium or a commercially pure titanium alloy. More preferably, the retaining screw 14 is formed of the titanium alloy Ti-6Al-4V (ASTM-F 136). In another preferred embodiment, the retaining screw 14 is formed of a palladium alloy. In yet another preferred embodiment, the retaining screw 14 is formed of a platinum alloy. In other preferred embodiments, the retaining screw 14 can be efficaciously formed of alternate materials, such as other alloys, metals, ceramics, plastics, as required or desired, giving due consideration to the goals of providing a suitably strong, light weight, biocompatible and/or corrosion resistant screw 14, and/or of achieving one or more of the benefits and advantages as taught or suggested herein.

The abutment 12 is preferably formed of titanium or a commercially pure titanium alloy. More preferably, the abutment 12 is formed of the titanium alloy Ti-6Al-4V. In other preferred embodiments, the abutment 12 can be efficaciously formed of alternate materials, such as other alloys, metals, ceramics, plastics, as required or desired, giving due consideration to the goals of providing a suitably strong, light weight, biocompatible and/or corrosion resistant abutment 12, and/or of achieving one or more of the benefits and advantages as taught or suggested herein.

The dental implant 16 is preferably formed of titanium or a commercially pure titanium alloy. More preferably, the implant 16 is formed of the titanium alloy Ti-6Al-4V. In other preferred embodiments, the implant 16 can be efficaciously formed of alternate materials, such as other alloys, metals, ceramics, plastics, as required or desired, giving due consideration to the goals of providing a suitably strong, light weight, biocompatible and/or corrosion resistant abutment 12, and/or of achieving one or more of the benefits and advantages as taught or suggested herein.

As the skilled artisan will appreciate, the retaining screw 14, the abutment 12 and the dental implant 16 can be dimensioned in a wide variety of manners taking into consideration the particular dental application and the needs of the patient, among other factors. In one example as illustrated herein, the screw 14 has a length of about 7.75 mm (0.305 inches) and a major diameter of about 2.49 mm (0.098 inches). The screw head 60 has a length of about 2.03 mm (0.08 inches) and a major diameter of about 2.49 mm (0.098 inches). The screw shank 62 has a length of about 5.72 mm (0.225 inches). The threaded portion 64 has a length of about 2.92 mm (0.115 inches), a major diameter of about 1.78 mm (0.07 inches) and a minor diameter of about 1.27 mm (0.05 inches). The upper non-threaded shank portion 68 has a length of about 2.16 mm (0.085 inches) and a diameter of about 1.27 mm (0.05 inches). The lower non-threaded shank portion 70 has a length of about 0.635 mm (0.025 inches) and a diameter of about 1.27 mm (0.05 inches). The skilled artisan will recognize that the screw 14 can be efficaciously dimensioned and configured in other manners, as required or desired, giving due consideration to the goals of providing high preload, and/or of achieving one or more of the benefits and advantages as taught or suggested herein.

Referring in particular to FIGS. 1 and 2, during assembly of the dental implant system 10 the abutment 12 is seated, placed or positioned on the implant 16 after the latter has osseointegrated with the bone material of the jawbone. At this stage, the abutment seating surface 24 is in contact with or abuts against the opposed implant seating surface 48. The abutment retaining screw 14 is inserted through the top opening 28 of the abutment cavity or passage 26 and threaded into the implant threaded socket 46 utilizing a suitable torque wrench or other tool. As the screw threaded portion 64, preferably coated with the low friction hard carbon coating 20 (FIG. 3), rotatingly engages the implant threaded socket 46, the screw head 60 moves farther into the abutment cavity 26 until the screw head contacting surface 72, preferably coated with the low friction hard carbon coating 20 (FIG. 3), abuts against or engages the abutment seating surface or shoulder 32.

As the screw 14 is further tightened or torqued, the screw head contacting surface 72 slides or rotates over or on the abutment seating surface 32 with a low level of frictional contact and improved lubriciousness. Moreover, the screw threaded portion 64 rotatingly engages the implant threaded socket 46 with a low level of frictional contact and improved lubriciousness. By reducing the friction between the rotating surfaces of the screw 14 and the opposed stationary bearing surfaces of the abutment 12 and implant 16, the preload on the screw 14 can be increased for a given applied torque because the torque causes the screw to be advanced further into the implant bore or socket 46. Advantageously, and as a result, this permits a large proportion of the applied torque to be converted into preloading of the abutment screw 14 and produces a high clamping force between the abutment 12 and the implant 16.

The dental screw 14 is tightened or torqued to a predetermined or preselected torque level or load below the yield point of the material, preferably titanium or a titanium alloy, comprising the screw 14. The prosthesis 18 is then be mounted on the abutment 12. The prosthesis 18 can be cemented to the abutment 12, or attached using another screw or bolt, or retained on the abutment 12 using a combination of cementing and screwing, as is needed or desired. A single tooth or multiple tooth restoration procedure may be performed, depending on the particular needs of the patient.

The hard carbon coated dental retaining screw of the present invention results in several advantages. The low friction surface finish provided by the hard carbon coating 20 (FIG. 3) causes a high preload to be built up in the screw 14 (FIGS. 1–2), and hence desirably results in a high clamping force between the abutment 12 and implant 14. Advantageously, this prevents and/or reduces the possibility of screw loosening and joint failure when subject to loads such as static loads, for example, during clinching, and/or cyclical loads or vibrations, for example, during mastication. Hence, the stability of the dental implant system 10 is improved and a secure and reliable fastening or coupling is provided between the abutment 12 and implant 16. Another advantage is that the high preload desirably improves the fatigue life of the screw 14.

The high preload (or clamping force) also facilitates in providing a reliable seal at the interface 76 (see FIG. 1) between the abutment seating surface 24 and the implant seating surface 48. Advantageously, this shields the interior of the implant system 10 from invasion by oral fluids, bacteria or other contaminants, and hence desirably protects the patient from infection.

Another advantage is due to the high mechanical surface hardness provided by the hard carbon coating 20. Thus, the coating 20 resists deformation during tightening of the screw 14, and hence protects the screw threaded portion 64 from possible "galling." Another advantage is that the hard carbon coating 20 is biocompatible. Yet another advantage is that the hard carbon coating 20 is chemically inert. A further advantage is that the hard carbon coating 20 has a high resistance to corrosion. Moreover, and advantageously, the hard carbon coating 20 is relatively inexpensive.

OTHER PREFERRED EMBODIMENTS

Figure 6:
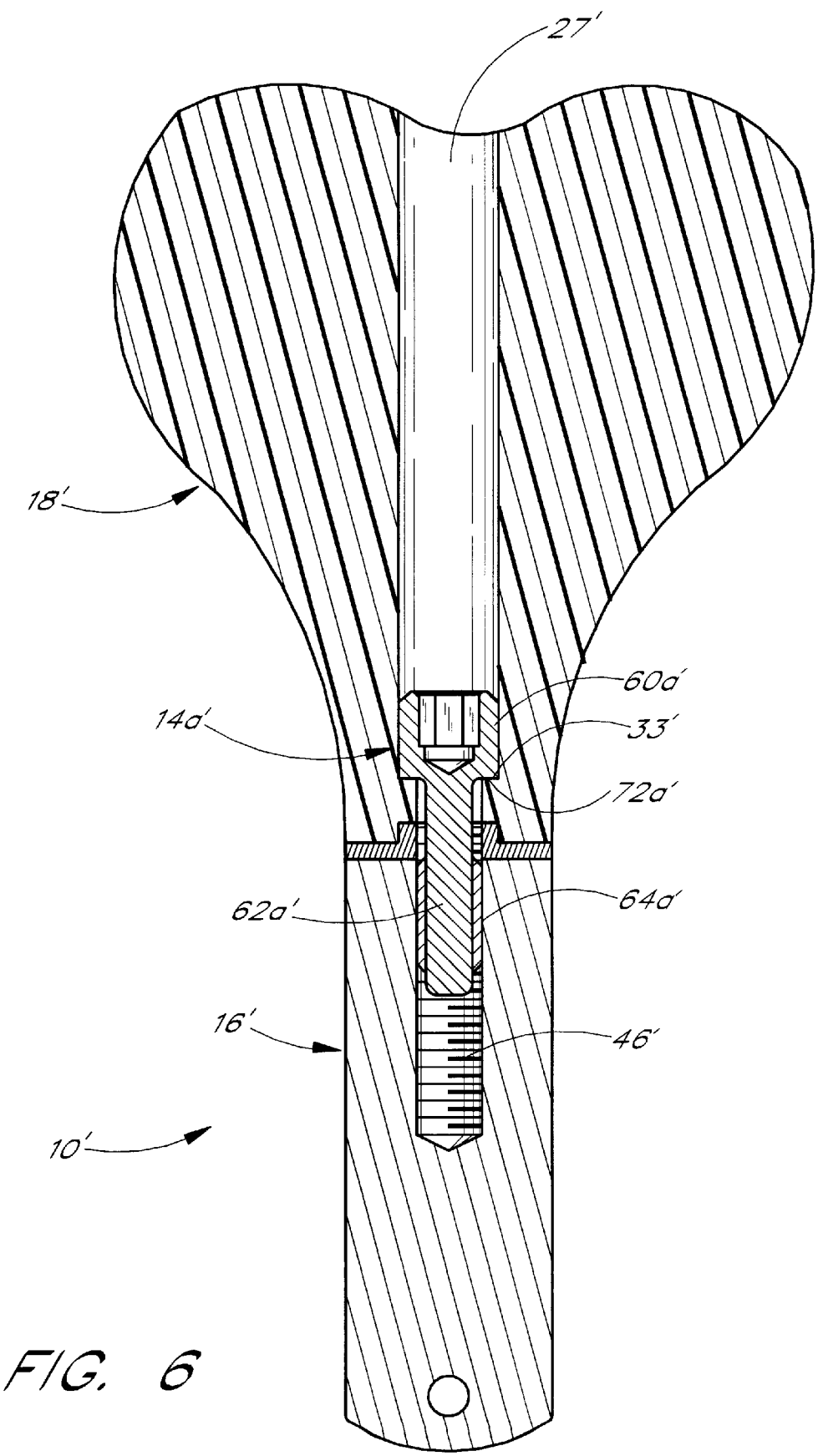
FIG. 6 is a cross-section view of a dental implant system having features in accordance with another preferred embodiment of the present invention.

FIG. 6 illustrates a dental prosthetic implant system, assembly, stack or combination 10' having features in accordance with another preferred embodiment of the present invention. The dental implant system 10' generally comprises a restoration retaining screw or bolt 14a' having a "hard carbon" low friction surface finish, a dental implant, fixture or root 16', and a dental restoration, prosthesis or artificial tooth 18'. In this embodiment, the prosthesis 18' is directly attached to the implant 16' using the securement screw 14a' without any intervening abutment. If needed or desired, cementing may also be used in conjunction with the retaining screw 14a' to secure the prosthesis 18' to the implant 16'.

The retaining screw 14a' is received in a cavity 27' of the prosthesis 18' and the threaded bore or socket 46' of the implant 16'. The seating or contacting surface 72a' of the screw head or cap 60a' abuts against a seating surface or shoulder 33' within the prosthesis cavity 27'. The threaded portion 64a' of the screw shank 62a' threadably engages the threaded socket 46' of the implant 16'.

Preferably, at least a portion of the dental retaining screw 14a' is coated with a hard carbon coating or film 20 (shown schematically in FIG. 3)—this coating on the screw 14a' provides some or all of the properties, characteristics, functions and/or advantages as taught or suggested hereinabove for any or all of the embodiments. The coating 20 can comprise, for example, a diamond-like carbon (DLC) coating 20, an amorphous diamond coating 20, a crystalline diamond coating 20, or a combination thereof. In one preferred embodiment, the coating 20 is a diamond-like carbon (DLC) coating 20. In another preferred embodiment the coating 20 comprises an amorphous diamond coating 20.

In one preferred embodiment, the screw head seating surface 72a' and the entire screw shank 62a' are coated with a hard carbon coating 20 (FIG. 3). In another preferred embodiment, the screw head seating surface 72a' and the screw threaded portion 64a' are coated with a hard carbon coating 20. In yet another preferred embodiment, the entire screw 14a' is coated with a hard carbon coating 20. In other preferred embodiments, various combinations of selected surfaces of the dental screw 14a' can be coated with hard carbon with efficacy, as required or desired, giving due consideration to the goals of providing increased preload, and/or of achieving one or more of the benefits and advantages as taught or suggested herein.

In general, a hard carbon coating or film, such as the diamond-like carbon (DLC) coating 20 (FIG. 3), may be applied to selected surfaces of the screw 14a', the prosthesis 18' and/or the implant 16' in a variety of configurations, as required or desired, giving due consideration to the goals of providing increased preload, and/or of achieving one or more of the benefits and advantages as taught or suggested herein. For example, the hard carbon coating 20 may be provided on the seating surface 33' of the prosthesis 18' and/or the threaded bore 46' of the implant 16' instead of on the retaining screw 14a' or in conjunction with the hard carbon coating 20 on the screw 14a'.

Figure 7:
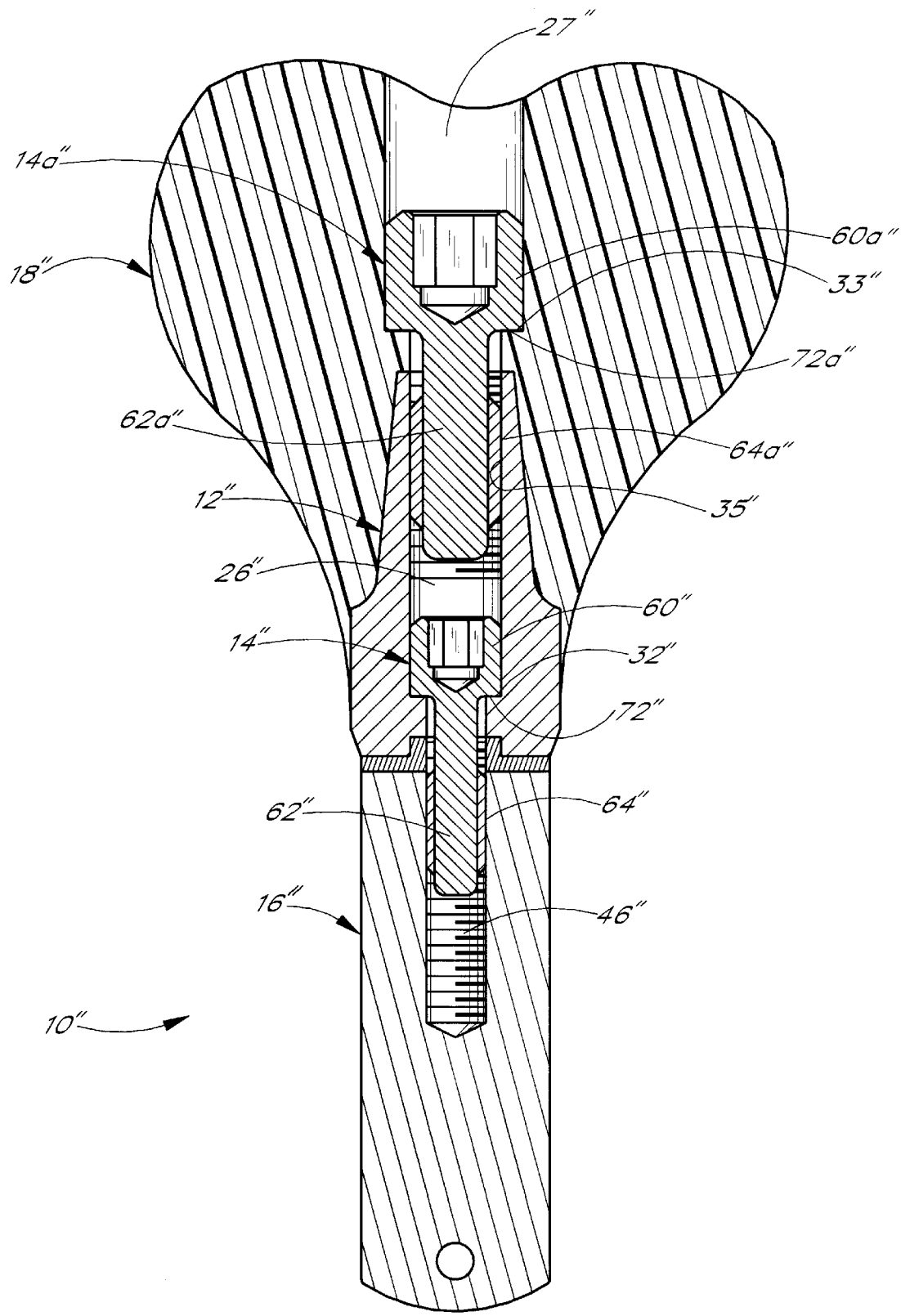
FIG. 7 is a cross-section view of a dental implant system having features in accordance with a further preferred embodiment of the present invention.

FIG. 7 illustrates a dental prosthetic implant system, assembly, stack or combination 10" having features in accordance with a further preferred embodiment of the present invention. The dental implant system 10" generally comprises an abutment 12", an abutment retaining screw or bolt 14" having a "hard carbon" low friction surface finish, a dental implant, fixture or root 16", a dental restoration, prosthesis or artificial tooth 18", and a restoration retaining screw or bolt 14a" having a "hard carbon" low friction surface finish. In this embodiment, two dental retaining screws 14", 14a" are used. The securement screw 14" fastens the abutment 12" to the implant 16" and the securement screw 14a" is used to attach the prosthesis 18" to the abutment 12". If needed or desired, cementing may also be used in conjunction with the retaining screw 14a" to secure the prosthesis 18" to the abutment 12".

The retaining screw 14" is received in the cavity 26" of the abutment 12" and the threaded bore or socket 46" of the implant 16". The seating or contacting surface 72" of the screw head or cap 60" abuts against the seating surface or shoulder 32" within the abutment cavity 26". The threaded portion 64" of the screw shank 62" threadably engages the threaded socket 46" of the implant 16".

Preferably, at least a portion of the abutment retaining screw 14" is coated with a hard carbon coating or film 20 (shown schematically in FIG. 3)—this coating on the screw 14" provides some or all of the properties, characteristics, functions and/or advantages as taught or suggested hereinabove for any or all of the embodiments. The coating 20 can comprise, for example, a diamond-like carbon (DLC) coating 20, an amorphous diamond coating 20, a crystalline diamond coating 20, or a combination thereof. In one preferred embodiment, the coating 20 is a diamond-like carbon (DLC) coating 20. In another preferred embodiment the coating 20 comprises an amorphous diamond coating 20.

In one preferred embodiment, the screw head seating surface 72" and the entire screw shank 62" are coated with a hard carbon coating 20 (FIG. 3). In another preferred embodiment, the screw head seating surface 72" and the screw threaded portion 64" are coated with a hard carbon coating 20. In yet another preferred embodiment, the entire screw 14" is coated with a hard carbon coating 20. In other preferred embodiments, various combinations of selected surfaces of the dental screw 14" can be coated with hard carbon with efficacy, as required or desired, giving due consideration to the goals of providing increased preload, and/or of achieving one or more of the benefits and advantages as taught or suggested herein.

In general, a hard carbon coating or film, such as the diamond-like carbon (DLC) coating 20 (FIG. 3), may be applied to selected surfaces of the screw 14", the abutment 12" and/or the implant 16" in a variety of configurations, as required or desired, giving due consideration to the goals of providing increased preload, and/or of achieving one or more of the benefits and advantages as taught or suggested herein. For example, the hard carbon coating 20 may be provided on the seating surface 32" of the abutment 12" and/or the threaded bore 46" of the implant 16" instead of on the retaining screw 14" or in conjunction with the hard carbon coating 20 on the screw 14".

Still referring to FIG. 7, the retaining screw 14a" is received in the cavity 27" of the prosthesis 18" and the cavity 26" of the abutment 12". The seating or contacting surface 72a" of the screw head or cap 60a" abuts against the seating surface or shoulder 33" within the prosthesis cavity 27". The abutment cavity 26" comprises an upper threaded portion, socket or bore 35". The threaded portion 64a" of the screw shank 62a" threadably engages the threaded socket 35" of the abutment 12".

Preferably, at least a portion of the prosthesis retaining screw 14a" is coated with a hard carbon coating or film 20 (shown schematically in FIG. 3)—this coating on the screw 14a" provides some or all of the properties, characteristics, functions and/or advantages as taught or suggested hereinabove for any or all of the embodiments. The coating 20 can comprise, for example, a diamond-like carbon (DLC) coating 20, an amorphous diamond coating 20, a crystalline diamond coating 20, or a combination thereof. In one preferred embodiment, the coating 20 is a diamond-like carbon (DLC) coating 20. In another preferred embodiment the coating 20 comprises an amorphous diamond coating 20.

In one preferred embodiment, the screw head seating surface 72a" and the entire screw shank 62a" are coated with a hard carbon coating 20 (FIG. 3). In another preferred embodiment, the screw head seating surface 72a" and the screw threaded portion 64a" are coated with a hard carbon coating 20. In yet another preferred embodiment, the entire screw 14a" is coated with a hard carbon coating 20. In other preferred embodiments, various combinations of selected surfaces of the dental screw 14a" can be coated with hard carbon with efficacy, as required or desired, giving due consideration to the goals of providing increased preload, and/or of achieving one or more of the benefits and advantages as taught or suggested herein.

In general, a hard carbon coating or film, such as the diamond-like carbon (DLC) coating 20 (FIG. 3), may be applied to selected surfaces of the screw 14a", the prosthesis 18" and/or the abutment 12" in a variety of configurations, as required or desired, giving due consideration to the goals of providing increased preload, and/or of achieving one or more of the benefits and advantages as taught or suggested herein. For example, the hard carbon coating 20 may be provided on the seating surface 33" of the prosthesis 18" and/or the threaded bore 35" of the abutment 12" instead of on the retaining screw 14a" or in conjunction with the hard carbon coating 20 on the screw 14a".

CONICAL SEATING SURFACES

Figure 8:
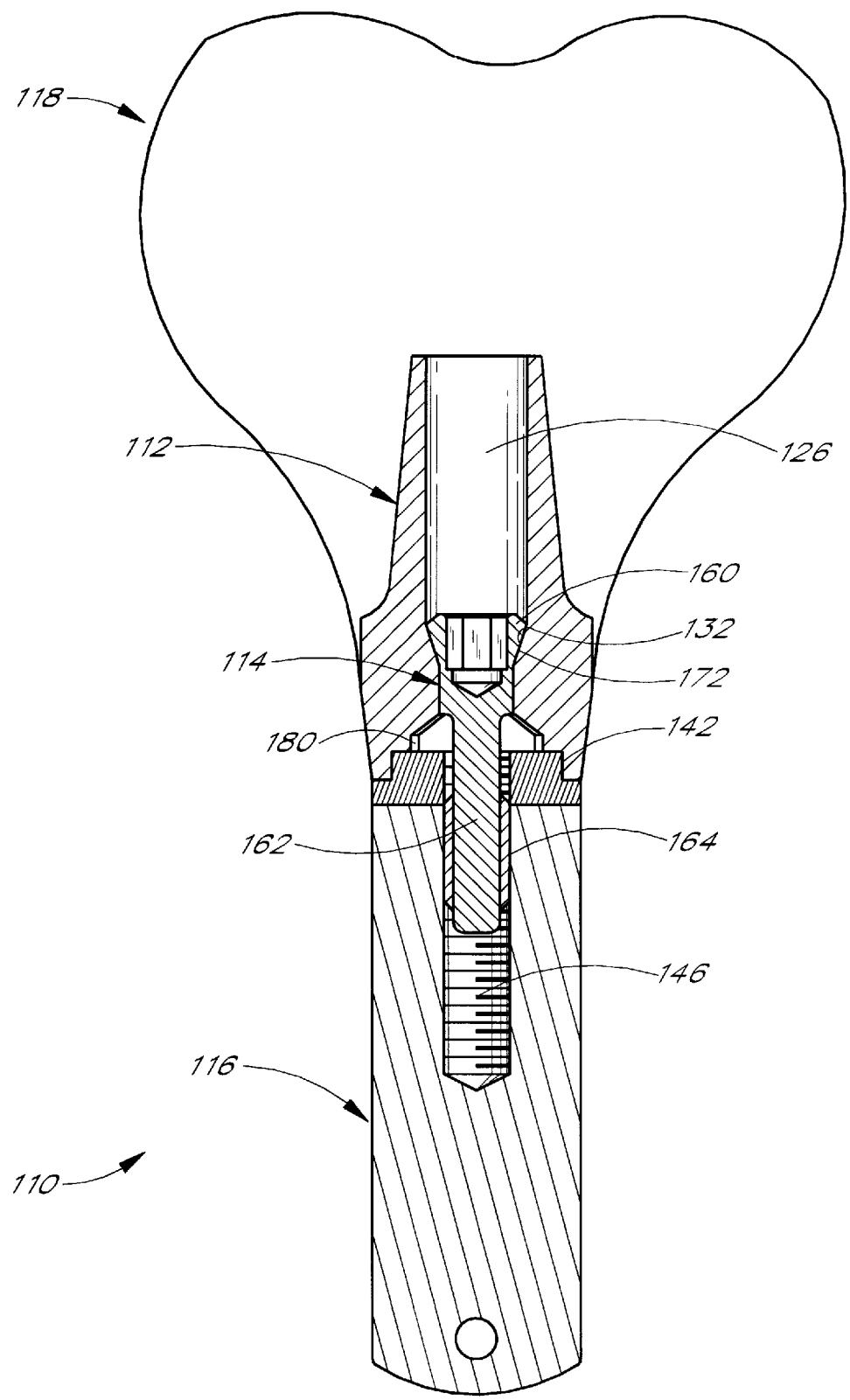
FIG. 8 is a partial cross-section view of a dental implant system having features in accordance with one preferred embodiment of the present invention.

FIG. 8 illustrates a dental prosthetic implant system, assembly, stack or combination 110 having features in accordance with one preferred embodiment of the present invention. The dental implant system 110 generally comprises an abutment 112, an abutment retaining screw or bolt 114, a dental implant, fixture or root 116 and a dental restoration, prosthesis or artificial tooth 118. The prosthesis 118 can be secured to the abutment 112 using a second retaining screw or bolt and/or utilizing cementing.

The retaining screw 114 is received in the cavity 126 of the abutment 112 and the threaded bore or socket 146 of the implant 116. Preferably, a tapered, conical or frusto-conical seating or contacting surface/portion 172 of the screw head or cap 160 abuts against an opposed tapered, conical or frusto-conical seating surface/portion 132 within the abutment cavity 126. The threaded portion 164 of the screw shank 162 threadably engages the threaded socket 146 of the implant 116. Advantageously, and as discussed later herein, the Morse taper on the seating surface 172 of the screw 114 and the seating surface 132 of the abutment assists in preventing or resisting screw loosening due to the wedging of the screw head tapered surface 172 in the abutment tapered surface 132.

Preferably, the taper or cone angle of the screw seating surface 172 and the abutment seating surface 132 is about 15° with respect to the longitudinal axis of the screw 114 and/or abutment 112. In other preferred embodiments, the taper or cone angle can be alternately selected with efficacy, as required or desired, giving due consideration to the goals of preventing or resisting screw loosening, and/or of achieving one or more of the benefits and advantages as taught or suggested herein.

Preferably, at least a portion of the abutment retaining screw 114 is coated with a hard carbon coating or film 20 (shown schematically in FIG. 3)—this coating on the screw 114 provides some or all of the properties, characteristics, functions and/or advantages as taught or suggested hereinabove for any or all of the embodiments. The coating 20 can comprise, for example, a diamond-like carbon (DLC) coating 20, an amorphous diamond coating 20, a crystalline diamond coating 20, or a combination thereof. In one preferred embodiment, the coating 20 is a diamond-like carbon (DLC) coating 20. In another preferred embodiment the coating 20 comprises an amorphous diamond coating 20.

In one preferred embodiment, the screw head tapered seating surface 172 and the entire screw shank 162 are coated with a hard carbon coating 20 (FIG. 3). In another preferred embodiment, the screw head tapered seating surface 172 and the screw threaded portion 164 are coated with a hard carbon coating 20. In yet another preferred embodiment, the entire screw head 160 is coated with a hard carbon coating 20. In a further preferred embodiment, the entire screw 114 is coated with a hard carbon coating 20. In other preferred embodiments, various combinations of selected surfaces of the. dental screw 114 can be coated with hard carbon with efficacy, as required or desired, giving due consideration to the goals of providing increased preload, and/or of achieving one or more of the benefits and advantages as taught or suggested herein.

In general, a hard carbon coating or film, such as the diamond-like carbon (DLC) coating 20 (FIG. 3), may be applied to selected surfaces of the screw 114, the abutment 112 and/or the implant 116 in a variety of configurations, as required or desired, giving due consideration to the goals of providing increased preload, and/or of achieving one or more of the benefits and advantages as taught or suggested herein. For example, the hard carbon coating 20 may be provided on the tapered seating surface 132 of the abutment 12 and/or the threaded bore 146 of the implant 116 instead of on the retaining screw 114 or in conjunction with the hard carbon coating 20 on the screw 114. Alternatively, or in addition, a low friction surface finish can be provided by a coating of a malleable biocompatible material such as gold, a gold alloy, silver, a silver alloy or anodic or anodized titanium, on selected surfaces, for example, the abutment tapered seating surface 132 and/or the screw head tapered seating surface 172.

The above also applies to a prosthesis retaining screw (not shown) used to secure the prosthesis 118 to the abutment 112 and/or implant 116. Thus, the head of the prosthesis retaining screw can include a tapered, conical or frusto-conical seating or contacting surface/portion to abut against an opposed tapered, conical or frusto-conical seating surface/portion of the prosthesis and the screw threads can engage female threads within the abutment cavity 126. Moreover, selected surfaces of the prosthesis retaining screw, the prosthesis 118 and/or the abutment 112 may be coated with a low friction hard carbon coating or other malleable biocompatible coating (as indicated above) with efficacy, as required or desired, giving due consideration to the goals of preventing or resisting screw loosening, and/or of achieving one or more of the benefits and advantages as taught or suggested herein.

In one preferred embodiment, and as shown in FIG. 8, an optional spring, lock or Belleville washer 180 is interposed between the screw head 160 (and abutment 112) and the implant 116. The spring washer 180 is seated on the implant post 142 and within the abutment cavity 126. The washer 180 acts like a spring and applies a generally constant tensile force on the abutment screw 114. This decreases the chance of loosening under cyclic or vibratory loads. The spring washer 180 acts as a damping mechanism for micromovement, preventing transmission of that movement into the screw 114.

A suitable lock, spring or Belleville washer can also be used in conjunction with a prosthesis retaining screw (not shown) used to secure the prosthesis 118 to the abutment 112. Moreover, one or more lock, spring or Belleville washers may be efficaciously utilized with any or all of the embodiments disclosed herein, as required or desired, giving due consideration to the goals of providing increased preload, and/or of achieving one or more of the benefits and advantages as taught or suggested herein.

The conical seating surface mechanism (wedged configuration or Morse taper) can be used as an auxiliary locking mechanism in conjunction with any or all of the embodiments disclosed herein or it can comprise an independent means for preventing or reducing screw loosening, as required or desired, giving due consideration to the goals of preventing or resisting screw loosening, and/or of achieving one or more of the benefits and advantages as taught or suggested herein.

Figure 9:
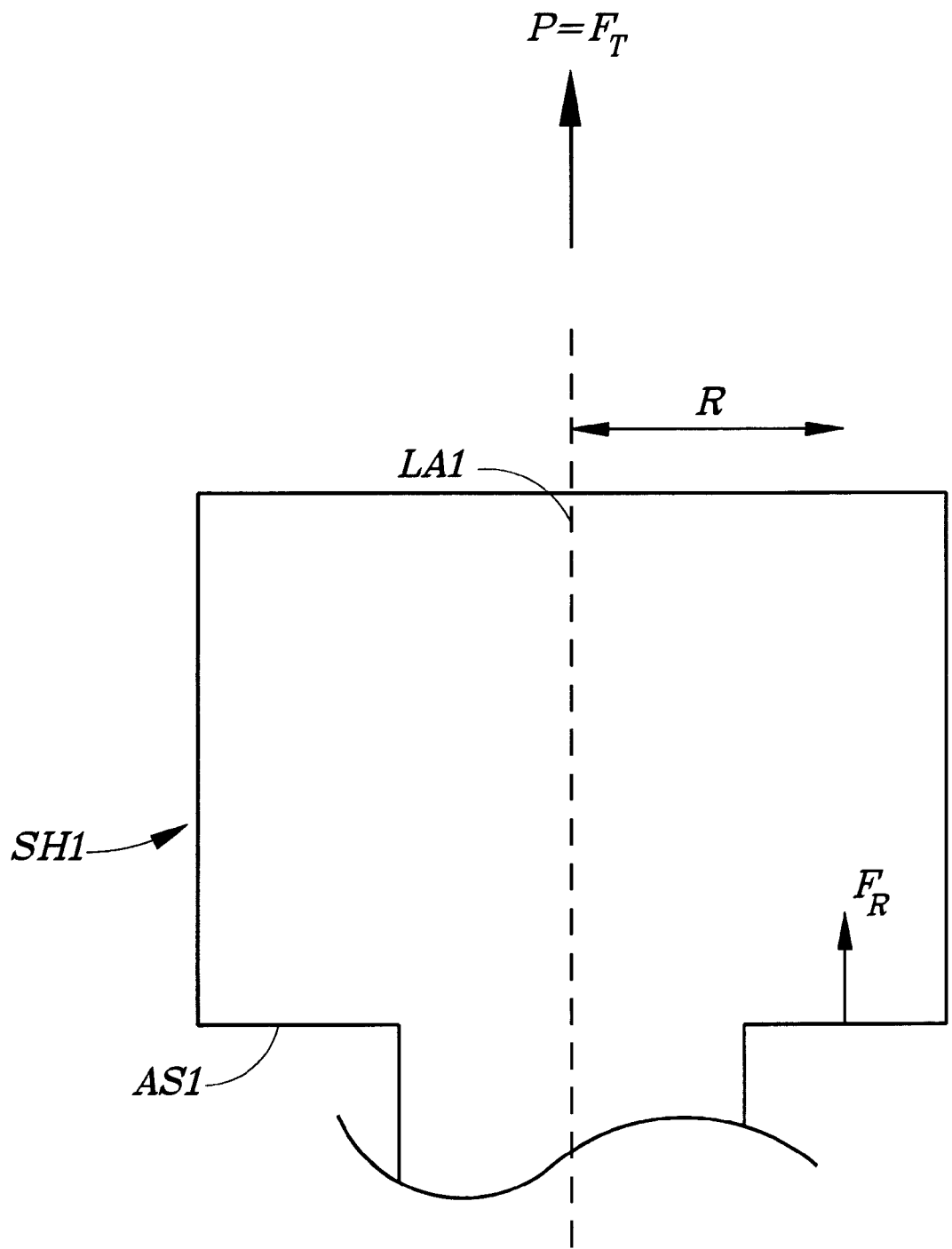
FIG. 9 is a simplified schematic force diagram of an axial seating surface screw head.
Figure 10:
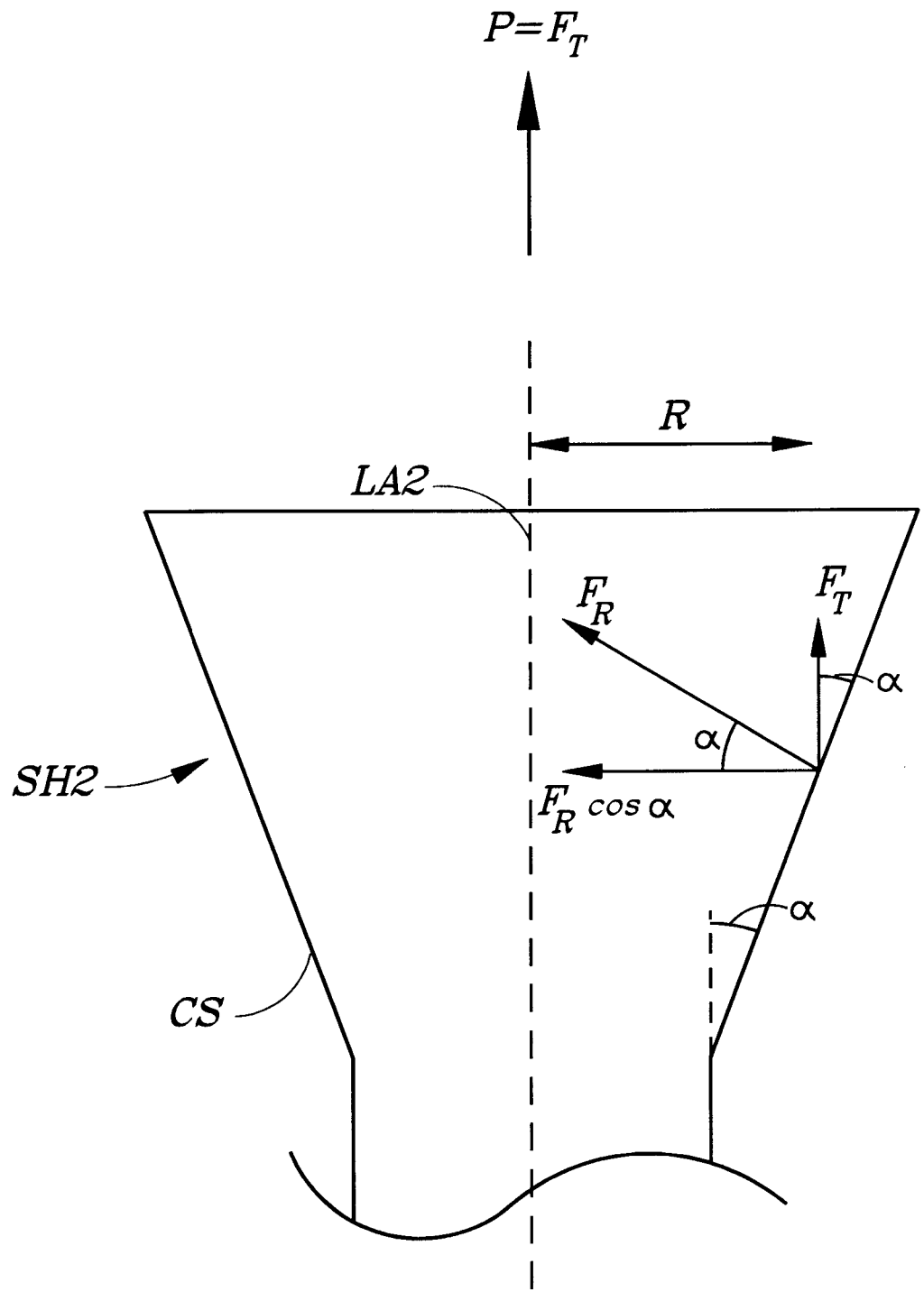
FIG. 10 is a simplified schematic force diagram of a conical seating surface screw head.

FIGS. 9 and 10 are simplified schematic force diagrams respectively of axial and conical seating surfaces. FIG. 9 schematically shows a screw head SH1 with an axial seating surface AS. After the screw has been "fully" engaged or tightened it exerts a tensile force $F_T$ which is substantially normal to the seating surface AS and generally parallel to the longitudinal axis LA1. The preload P is equal to this tensile force, so that $P=F_T$. The tensile force or preload is equal to the normal reaction force $F_R$ which is acting on the screw. This reaction force $F_R$ generates a frictional force F which is equal in magnitude to $\mu F_R = \mu F_T = \mu P$, where $\mu$ is the coefficient of friction. This frictional force is the sum of all the small forces, each of which is acting at one of the almost infinite number of contact points between the screw and abutment (or other component). The resultant frictional force can generally be taken as acting tangentially at the mean radius R of the two contacting faces, which in this case is the mean radius of the annular seating surface of the screw. Consequently, the removal torque Q that has to be overcome to cause slip can be estimated by the expression:

$$Q = \mu PR \text{ (axial seating surface)}$$

FIG. 10 schematically shows a screw head SH2 with a conical seating surface CS and a longitudinal axis LA2. Once the screw has been "fully" engaged or tightened it exerts a tensile force $F_T$ which is substantially generally parallel to the longitudinal axis LA1. The preload P is equal to this tensile force, so that $P=F_T$. The tensile force or preload is equal to the vertical component (or component parallel to the longitudinal axis LA2) of the normal reaction force $F_R$ which is acting on the screw. Thus, for a cone angle $\alpha$ (with respect to the screw longitudinal axis LA2), $F_T = F_R \sin\alpha$. The resultant frictional force F is equal in magnitude to $\mu F_R = \mu F_T/\sin\alpha = \mu P/\sin\alpha$, where $\mu$ is the coefficient of friction. The resultant frictional force can generally be taken as acting tangentially at the mean radius R of the two contacting faces, which in this case is the mean radius of the tapered seating surface of the screw. Consequently, the removal torque Q that has to be overcome to cause slip can be estimated by the expression:

$$Q = \left(\frac{1}{\sin\alpha}\right)\mu PR \text{ (conical seating surface)}$$

Thus, for a given coefficient of friction $\mu$, a given preload P, and a given moment arm R, the removal torque is augmented by a factor of $(1/\sin\alpha)$ for the conical seating surfaces due to the wedging action of the cones or Morse taper configuration. For a typical taper or cone angle cc of about 15°, $(1/\sin\alpha)=3.86$, and hence the torsional resistance to slip for the conical seating surfaces compared to the axial seating surfaces is greater by a factor of about 3 to 4 times.

Figure 11:
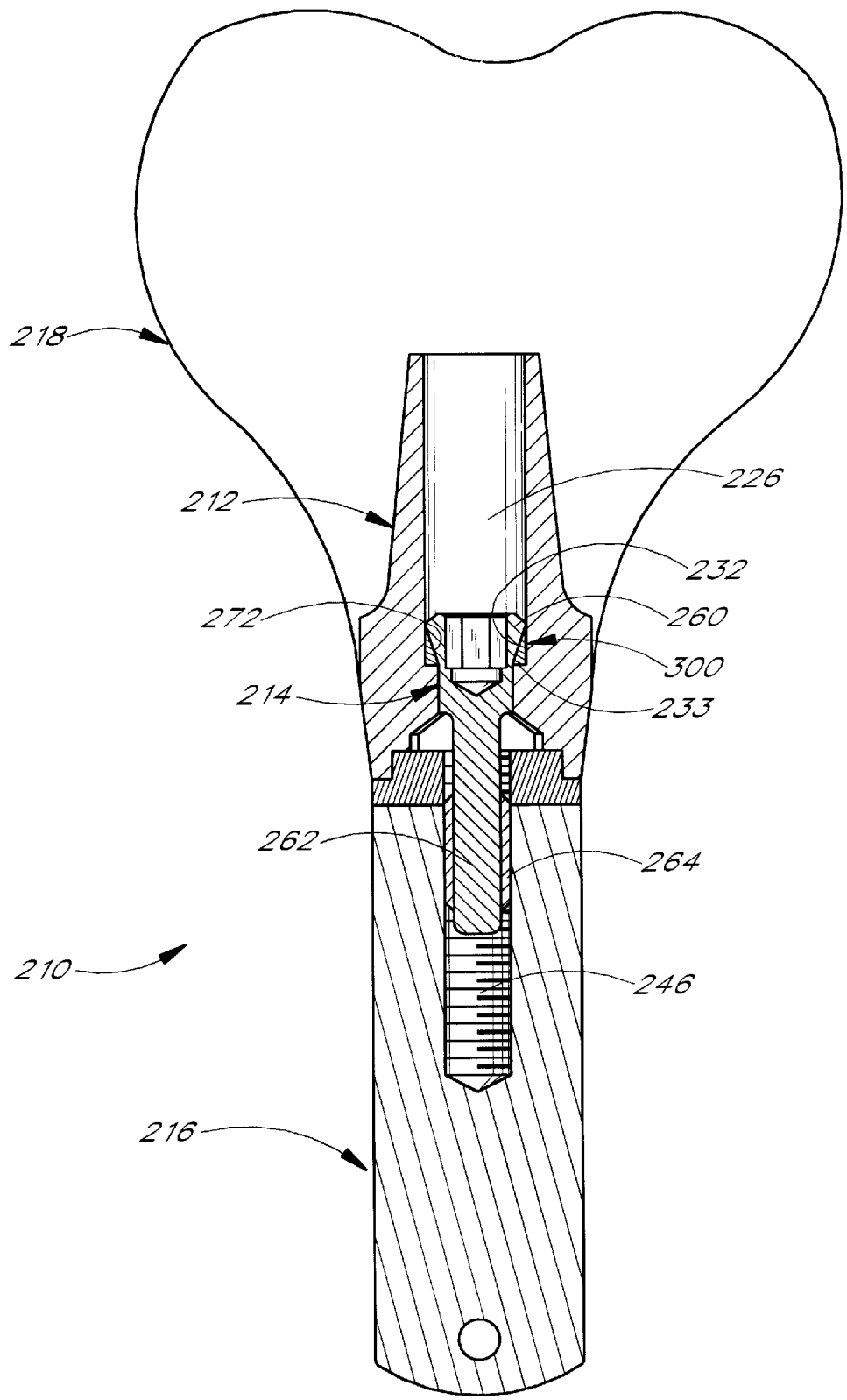
FIG. 11 is a partial cross-section view of a dental implant system having features in accordance with another preferred embodiment of the present invention.

FIG. 11 illustrates a dental prosthetic implant system, assembly, stack or combination 210 having features in accordance with another preferred embodiment of the present invention. The dental implant system 210 generally comprises an abutment 212, an abutment retaining screw or bolt 214, a washer 300, a dental implant, fixture or root 216 and a dental restoration, prosthesis or artificial tooth 218. In this embodiment, the tapered seating surface of the abutment is replaced by the tapered, conical or frusto-conical washer 300. The prosthesis 218 can be secured to the abutment 212 using a second retaining screw or bolt and/or utilizing cementing.

Figure 12:
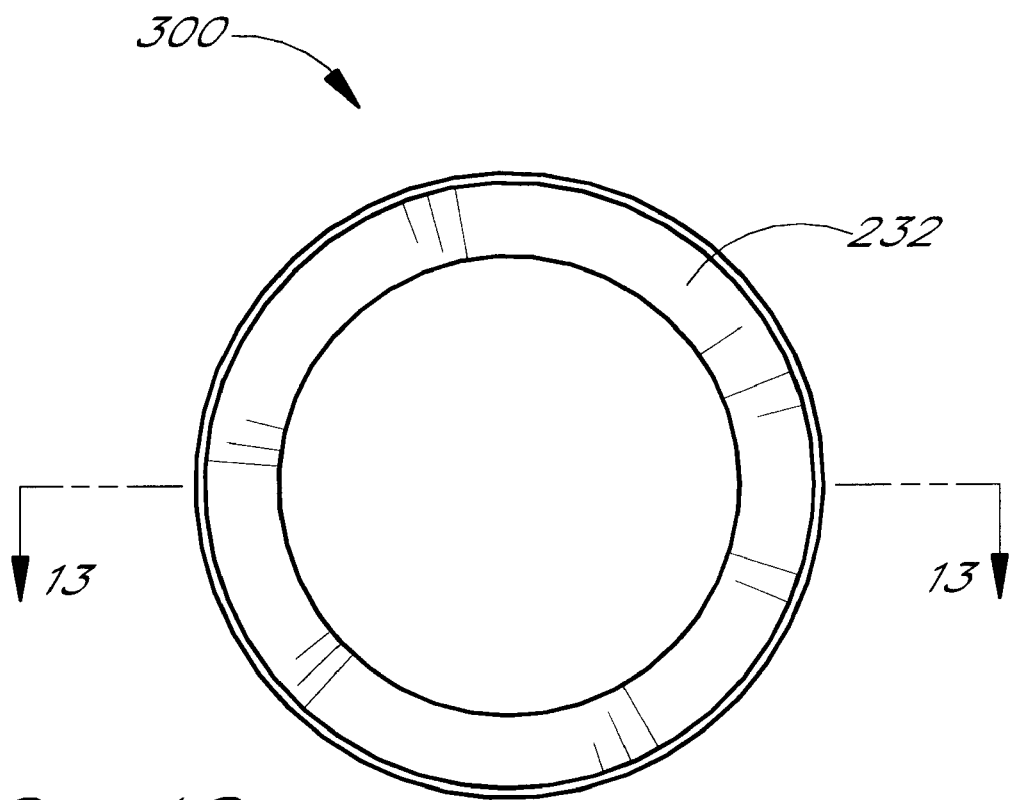
FIG. 12 is a top plan view of a conical washer of the dental implant system of FIG. 12.
Figure 13:
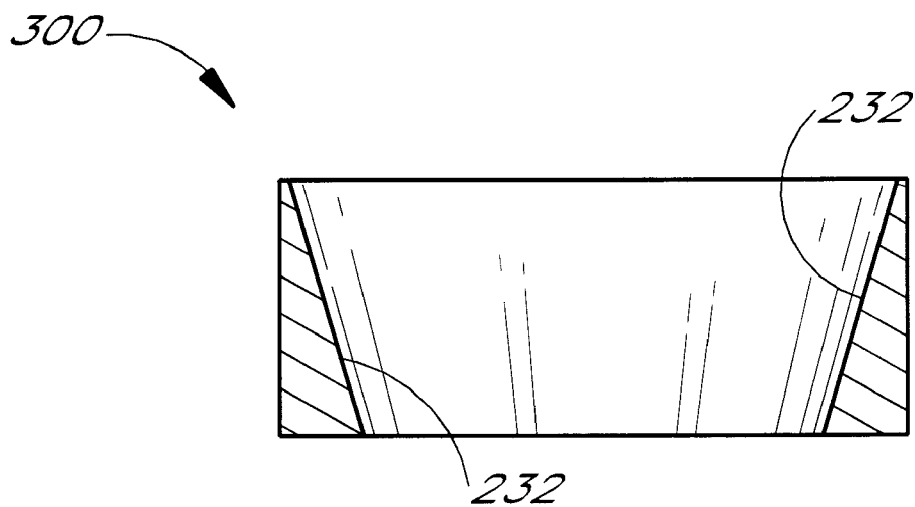
FIG. 13 is a cross-section view along line 13—13 of FIG. 12.

The retaining screw 214 is received in the cavity 226 of the abutment 212 and the threaded bore or socket 246 of the implant 216. Preferably, a tapered, conical or frusto-conical seating or contacting surface/portion 272 of the screw head or cap 260 abuts against an opposed tapered, conical or frusto-conical seating surface/portion 232 of the washer 300 (also shown in FIGS. 12 and 13). The washer 300 is interposed between the screw head seating surface 272 and the abutment 212 and is seated on a shoulder, ledge or seat 233 within the abutment cavity 226. The threaded portion 264 of the screw shank 262 threadably engages the threaded socket 246 of the implant 216. Advantageously, and as discussed above, the Morse taper on the seating surface 272 of the screw 214 and the seating surface 272 of the washer 300 assists in preventing or resisting screw loosening due to the wedging of the screw head tapered surface 272 in the washer tapered surface 232.

Preferably, the taper or cone angle of the screw seating surface 272 and the washer seating surface 232 is about 15° with respect to the longitudinal axis of the screw 214 and/or washer 300. In other preferred embodiments, the taper or cone angle can be alternately selected with efficacy, as required or desired, giving due consideration to the goals of preventing or resisting screw loosening, and/or of achieving one or more of the benefits and advantages as taught or suggested herein.

The washer 300 preferably has an outer diameter of about 2.57 mm (0.101 inches), an inner major diameter of about 2.44 mm (0.096 inches), an inner minor diameter of about 1.93 mm (0.076 inches) and a height of about 1.07 mm (0.042 inches). In other preferred embodiments, the washer 300 can be efficaciously dimensioned and configured in alternate manners, as required or desired, giving due consideration to the goals of preventing or resisting screw loosening, and/or of achieving one or more of the benefits and advantages as taught or suggested herein.

Preferably, at least a portion of the abutment retaining screw 214 and/or washer 300 is coated with a hard carbon coating or film 20 (shown schematically in FIG. 3)—this coating on the screw 214 provides some or all of the properties, characteristics, functions and/or advantages as taught or suggested hereinabove for any or all of the embodiments. The coating 20 can comprise, for example, a diamond-like carbon (DLC) coating 20, an amorphous diamond coating 20, a crystalline diamond coating 20, or a combination thereof. In one preferred embodiment, the coating 20 is a diamond-like carbon (DLC) coating 20. In another preferred embodiment the coating 20 comprises an amorphous diamond coating 20.

In one preferred embodiment, the screw head tapered seating surface 272 and the entire screw shank 262 are coated with a hard carbon coating 20 (FIG. 3). In another preferred embodiment, the screw head tapered seating surface 272 and the screw threaded portion 264 are coated with a hard carbon coating 20. In yet another preferred embodiment, the entire screw head 260 is coated with a hard carbon coating 20. In a further preferred embodiment, the entire screw 214 is coated with a hard carbon coating 20. In other preferred embodiments, various combinations of selected surfaces of the dental screw 214 can be coated with hard carbon with efficacy, as required or desired, giving due consideration to the goals of providing increased preload, and/or of achieving one or more of the benefits and advantages as taught or suggested herein.

In general, a hard carbon coating or film, such as the diamond-like carbon (DLC) coating 20 (FIG. 3), may be applied to selected surfaces of the screw 214, the washer 300 and/or the implant 116 in a variety of configurations, as required or desired, giving due consideration to the goals of providing increased preload, and/or of achieving one or more of the benefits and advantages as taught or suggested herein. For example, the hard carbon coating 20 may be provided on the tapered seating surface 232 of the washer 300 and/or the threaded bore 246 of the implant 216 instead of on the retaining screw 214 or in conjunction with the hard carbon coating 20 on the screw 214.

In one preferred embodiment, the washer 300 comprises a malleable biocompatible material such as gold, a gold alloy, silver or a silver alloy. Such a malleable washer 300 acts as a solid lubricant, and hence reduces the friction between the screw head 260 and the washer 300 during tightening of the screw 214. Advantageously, this results in a higher preload and a greater clamping force between the abutment 212 and implant 216. The malleable low friction washer 300 can be efficaciously used with an uncoated titanium screw 214 or with a hard carbon coated screw 214, as required or desired, giving due consideration to the goals of providing increased preload, and/or of achieving one or more of the benefits and advantages as taught or suggested herein.

In another preferred embodiment, the washer 300 comprises titanium or a titanium alloy and has a titanium anodic or anodized coating. Such a coating is disclosed in U.S. Pat. No. 5,833,463 to Hurson, incorporated by reference herein. The malleable anodized coating acts as a solid lubricant, and hence reduces the friction between the screw head 260 and the washer 300 during tightening of the screw 214. Advantageously, this results in a higher preload and a greater clamping force between the abutment 212 and implant 216. The anodized titanium coated washer 300 can be efficaciously used with an uncoated titanium screw 214 or with a hard carbon coated screw 214, as required or desired, giving due consideration to the goals of providing increased preload, and/or of achieving one or more of the benefits and advantages as taught or suggested herein.

The above also applies to a prosthesis retaining screw (not shown) used to secure the prosthesis 218 to the abutment 212 and/or implant 216. Thus, the head of the prosthesis retaining screw can include a tapered, conical or frusto-conical seating or contacting surface/portion to abut against an opposed tapered, conical or frusto-conical seating surface/portion of a washer and the screw threads can engage female threads within the abutment cavity 226. The washer can also comprise a suitable malleable biocompatible material as discussed above. Moreover, selected surfaces of the prosthesis retaining screw, the washer, the prosthesis 218 and/or the abutment 212 may be coated with a low friction hard carbon coating or other malleable biocompatible coating (as indicated above) with efficacy, as required or desired, giving due consideration to the goals of preventing or resisting screw loosening, and/or of achieving one or more of the benefits and advantages as taught or suggested herein.

The skilled artisan will recognize the utility of the present invention. The low friction hard carbon coating can be applied to a variety of dental retaining screws (and/or other associated components) to provide a reliable securement system for stacking dental components such as abutments and artificial teeth. The retaining screws can be used in conjunction with a wide variety of abutments, implants, dental restorations and/or other associated components.

While the components and techniques of the present invention have been described with a certain degree of particularity, it is manifest that many changes may be made in the specific designs, constructions and methodology hereinabove described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A retaining screw for fastening a dental component to an implant osseointegrated in a jawbone, comprising:
    a head comprising a seating surface sized and configured to engage a seating surface of said dental component and a cavity adapted to receive a tool for tightening said screw;
    a shank in mechanical communication with said head and comprising threads thereon adapted to threadably engage a threaded socket of said implant; and
    a coating comprising amorphous hard carbon and applied to at least said seating surface of said head to provide a low friction surface finish thereon.

2. The retaining screw of claim 1, wherein at least a portion of said shank is coated with hard carbon.

3. The retaining screw of claim 1, wherein said threads on said shank have said coating applied thereon.

4. The retaining screw of claim 1, wherein said coating comprises diamond-like carbon (DLC).

5. The retaining screw of claim 1, wherein said coating comprises amorphous diamond.

6. The retaining screw of claim 1, wherein said coating comprises two or more of diamond-like carbon (DLC), amorphous diamond, and crystalline diamond.

7. The retaining screw of claim 1, wherein said coating comprises a major proportion of $sp^3$ bonding.

8. The retaining screw of claim 1, wherein said coating is hydrogenated.

9. The retaining screw of claim 1, wherein said coating has a thickness in the range from about 0.5 μm to about 2.5 μm.

10. The retaining screw of claim 1, wherein said coating has a coefficient of friction of about 0.15.

11. The retaining screw of claim 1, wherein said seating surface of said head is substantially conical.

12. The retaining screw of claim 11, in combination with a washer having a substantially conical seating surface to engage said seating surface of said head.

13. A dental implant system for supporting a prosthesis, comprising:
    the retaining screw as recited in claim 1;
    a dental implant comprising a root portion and a threaded socket engaged with said threads of said retaining screw; and
    an abutment substantially irrotationally coupled with said implant and comprising a seating surface engaged with said seating surface of said head of said retaining screw to fasten said abutment to said dental implant.

14. The retaining screw of claim 13, wherein said hard carbon comprises between about 5 to about 35 atomic % hydrogen.

15. The retaining screw of claim 13, wherein said dental implant system further comprises a prosthesis.

16. The retaining screw of claim 15, wherein said dental implant system further comprises a securement screw having a hard carbon coating and engaged with said prosthesis and said abutment to fasten said prosthesis to said abutment.

17. The retaining screw of claim 13, wherein said dental implant system further comprises a spring washer interposed between said head of said retaining screw and said dental implant.

18. The retaining screw of claim 13, wherein said coating is formed by physical vapor deposition (PVD) and/or chemical vapor deposition.

19. The retaining screw of claim 13, wherein said coating has a thickness of about 1 μm.

20. The retaining screw of claim 13, wherein said hard carbon comprises between about 70% to about 100% $sp^3$ bonding.

21. An abutment securement system to fasten dental components in a stack, comprising a film of diamond-like carbon (DLC) applied to a seating surface of a screw and/or to a seat of an abutment to reduce friction between the seating surface and the seat, and thereby to provide improved preloading of said screw.

22. The abutment securement system of claim 21, in combination with an implant with said abutment secured to said implant.

23. The abutment securement system of claim 21, wherein said screw comprises a diamond-like carbon (DLC) coated threaded portion.

24. The abutment securement system of claim 21, wherein said film has a thickness of about 1 μm.

25. The abutment securement system of claim 21, wherein said film has a Knoop hardness of about 2000 $kg/mm^2$.

26. The abutment securement system of claim 21, wherein said seating surface of said screw is substantially frusto-conical.

27. The abutment securement system of claim 21, wherein said seat of said abutment is substantially frusto-conical.

28. A dental implant stack for supporting an oral restoration, comprising:
   an implant comprising a body portion adapted to be received in an alveolar cavity and an internal threaded bore;
   an abutment comprising a through cavity having a shoulder formed therein and seated on said implant;
   a dental screw comprising a threaded portion engaged with said threaded bore of said implant and a cap having a seating surface abutting against said shoulder of said abutment; and
   a coating of amorphous hard carbon on said seating surface of said dental screw to reduce friction and provide a high clamping force between said implant and said abutment.

29. The dental implant stack of claim 28, wherein said threaded portion of said dental screw is coated with an amorphous hard carbon coating.

30. The dental implant stack of claim 28, wherein said amorphous hard carbon comprises diamond-like carbon (DLC).

31. The dental implant stack of claim 28, wherein said amorphous hard carbon comprises amorphous diamond.

32. The dental implant stack of claim 28, wherein said dental screw comprises titanium or a titanium alloy.

33. The dental implant stack of claim 28, further comprising a restoration supported on said abutment.

34. The dental implant stack of claim 33, further comprising a securement screw engaged with said restoration and said abutment to fasten said restoration to said abutment.

35. The dental implant stack of claim 34, wherein said securement screw is coated with an amorphous hard carbon coating.

36. The dental implant stack of claim 34, wherein said securement screw comprises titanium or a titanium alloy.

37. A dental prosthetic assembly, comprising:
   a dental implant adapted for osseointegration in a jawbone and having a threaded socket originating from a top end;
   a dental component in abutting contact with said implant and having an internal seating surface;
   a securement bolt having a threaded portion engaged with said threaded socket of said implant; and
   a film comprising amorphous diamond on said threaded portion of said securement bolt and/or said threaded socket of said implant to reduce the coefficient of friction between said threaded portion of said securement bolt and said threaded socket of said implant.

38. The dental prosthetic assembly of claim 37, wherein said securement bolt comprises a seating surface and one or both of said seating surface of said securement bolt and said seating surface of said dental component are coated with an amorphous diamond film.

39. The dental prosthetic assembly of claim 38, wherein said dental component comprises an abutment.

40. The dental prosthetic assembly of claim 38, wherein said dental component comprises an implant.

41. The dental prosthetic assembly of claim 37, wherein said film has a coefficient of friction of about 0.15.

42. The dental prosthetic assembly of claim 37, wherein said film has a coefficient of friction in the range from about 0.1 to about 0.2.

43. A dental prosthetic implant system for supporting an artificial tooth, comprising:
   an implant having a post at a top end and a threaded bore originating therefrom;
   an abutment having an internal passage with a shoulder therein and a socket at a bottom end substantially irrotationally engaged with said post of said implant;
   a washer seated on said shoulder of said passage of said abutment and having a conical seating surface;
   a screw comprising a threaded portion engaged with said threaded bore of said implant and a head having a tapered surface abutting against said conical seating surface of said washer; and
   a film comprising amorphous hard carbon applied to the threaded portion of said screw and/or the threaded bore of said implant to reduce friction therebetween and provide improved preloading.

44. The dental prosthetic implant system of claim 43, wherein said washer is coated with a hard carbon coating.

45. The dental prosthetic implant system of claim 43, wherein said washer comprises a malleable biocompatible material.

46. The dental prosthetic implant system of claim 43, wherein said washer comprises gold.

47. The dental prosthetic implant system of claim 43, wherein said washer comprises a gold alloy.

48. The dental prosthetic implant system of claim 43, wherein the taper angle of said conical seating surface of said washer is about 15°.

49. The dental prosthetic implant system of claim 43, wherein said tapered surface of said screw is coated with a hard carbon coating.

50. A method of forming a dental stack for supporting a prosthesis, comprising the steps of:

placing a first dental component having an internal cavity on a second dental component having a threaded bore;

inserting a retaining screw through said cavity of said first dental component to threadably engage said threaded bore of said second dental component, said retaining screw having a coating of amorphous hard carbon formed thereon to reduce friction; and tightening said retaining screw to a predetermined or preselected torque to fasten said first dental component to said second dental component.

51. The method of claim 50, further comprising the step of abutting a seating surface of said retaining screw against a hard carbon coated shoulder of said cavity of said first dental component.

52. The method of claim 50, further comprising the step of seating a malleable washer on a shoulder of said cavity of said first dental component to engage a tapered seating surface of said retaining screw.

53. A method of increasing the preload on a screw used to secure dental components, comprising the steps of:

seating a dental component having an internal shoulder on an implant having a threaded socket and osseointegrated in a jawbone;

threading a screw in said threaded socket of said implant and seating a head of said screw against said shoulder of said dental component, wherein a diamond-like carbon coating is provided on said head of said screw and/or said shoulder of said dental component to reduce friction; and torqing said screw using a tool to a predetermined or preselected load.

54. A method of making a retaining screw for securing and assembling dental components in a stack, comprising the steps of:

providing a cap portion on said retaining screw so that said cap portion has a seating surface and a cavity adapted to receive a tool for tightening said screw;

providing a shank portion on said retaining screw so that said shank portion has threads thereon; and forming an amorphous hard carbon coating on at least said seating surface of said cap portion to provide improved preloading.

55. The method of claim 54, further comprising the step of forming an amorphous hard carbon coating on said threads of said shank portion.

56. The method of claim 54, further comprising the step of forming an amorphous hard carbon coating on said shank portion.

57. The method of claim 54, wherein said step of forming an amorphous hard carbon coating comprises the step of physical vapor deposition (PVD).

58. The method of claim 54, wherein said step of forming an amorphous hard carbon coating comprises the step of chemical vapor deposition (CVD).

* * * * *